United States Patent [19]

Abe et al.

[11] Patent Number: 5,679,790
[45] Date of Patent: Oct. 21, 1997

[54] 2-[1-(1,3-THIAZOLIN-2-YL)AZETIDIN-3-YL] THIO-CARBAPENEM DERIVATIVES

[75] Inventors: Takao Abe, Sakado; Takeshi Isoda, Sayama; Chisato Sato, Kamifukuoka; Ado Mihira, Asaka; Satoshi Tamai, Kawasaki; Toshio Kumagai, Kawagoe, all of Japan

[73] Assignee: Lederle (Japan), Ltd., Tokyo, Japan

[21] Appl. No.: 631,224

[22] Filed: Apr. 12, 1996

Related U.S. Application Data

[62] Division of Ser. No. 267,397, Jun. 29, 1994, Pat. No. 5,534,510.

[30] Foreign Application Priority Data

| Jul. 1, 1993 | [JP] | Japan | 5-213306 |
| Mar. 28, 1994 | [JP] | Japan | 6-79320 |
| May 12, 1994 | [JP] | Japan | 6-122046 |

[51] Int. Cl.$^6$ .................................................. C07D 487/04
[52] U.S. Cl. .................................................. 540/350
[58] Field of Search .................................................. 540/350

[56] References Cited

U.S. PATENT DOCUMENTS 5,102,997  4/1992  Sugimura et al. .................. 540/350

FOREIGN PATENT DOCUMENTS

| 0 160 391 | 11/1985 | European Pat. Off. . |
| 01 61 541 | 11/1985 | European Pat. Off. . |
| 93/23402 | 11/1993 | WIPO . |

OTHER PUBLICATIONS

Patent Abstracts of Japan, vol. 13, No. 63, Feb. 13, 1989, JP 63-255280.

*Primary Examiner*—Rebecca Cook
*Attorney, Agent, or Firm*—Foley and Lardner

[57] ABSTRACT

Novel carbapenem compounds, (1R,5S,6S)-2-[1-(1,3-thiazolin-2-yl)azetidin-3-yl]thio-6-[(R)-1-hydroxyethyl]-1-methyl-carbapen-2-em-3-carboxyic acid derivatives.

These carbapenem compounds are represented by the following formula having a beta-coordinated methyl group introduced at the 1-position and a [1-(1,3-thiazolin-2-yl)azetidin-3-yl]thio group introduced at the 2-position.

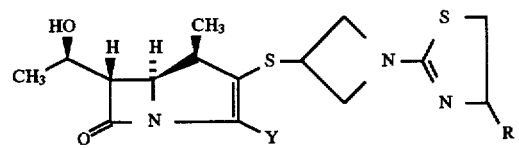

In the formula,

R is hydrogen; lower alkyl group which is unsubstituted or substituted by hydroxy, lower alkoxy or lower alkoxy-lower alkoxy group; group —COOR$^1$ (R$^1$ is hydrogen or lower alkyl group); or group —CONR$^2$R$^3$ (R$^2$ and R$^3$ are, independently each other, hydrogen or lower alkyl), and Y is carboxy, —COO$^\ominus$ or protected carboxy.

These compounds are useful antibiotics for prevention and treatment of bacterial infections.

2 Claims, No Drawings

2-[1-(1,3-THIAZOLIN-2-YL)AZETIDIN-3-YL] THIO-CARBAPENEM DERIVATIVES

This application is a division of application Ser. No. 08/267,397, filed Jun. 29, 1994 now U.S. Pat. No. 5,534,510.

BACKGROUND OF THE INVENTION

1. Field of the Invention

The present invention relates to carbapenem antibiotics and, more particularly, to 1β-methyl-carbapenem derivatives having a methyl group introduced at the 1-position and [1-(1,3-thiazolin-2-yl)azetidin-3-yl]thio group introduced at the 2-position of the carbapenem skeleton, and to antibacterial compositions containing the same as an active ingredient.

2. Description of the Prior Art

Prior art antibacterial carbapenemes including carba-2-penem-3-carboxylic acid represented by the following formula (A):

For example, an initial generation of carbapenem antibiotics is a naturally occurring carbapenem compound such as thienamycin represented by the formula (B):

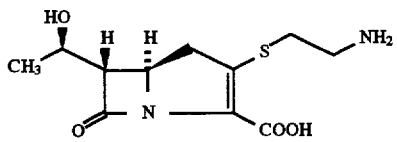

The thienamycin may be obtained from a fermentation broth of *Streptomyces cattleya* and has a broad range of antibacterial spectra against Gram-positive and Gram-negative bacteria. A prior art compound is imipenem (INN) represented by the following formula (C):

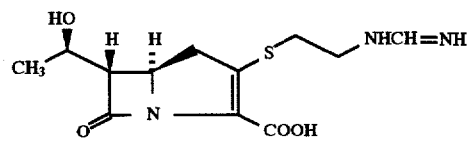

This compound is a practically available antibacterial agent and may be obtained by converting an amino group as a side chain at the 2-position to a formimidoyl group.

The imipenem of the formula (C) exhibits antibacterial activities higher than those of the thienamycin and ensures some degree of chemical stability; however, it presents the disadvantage that it is decomposed within a short period of time by kidney dehydropeptidase (DHP) in the living body. For this reason, it cannot be administered singly, and must be used in combination with a DHP inhibitor in order to control its decomposition leading to inactivation. Its formulation for clinical administration is a combination with cilastatin (INN) that is a DHP inhibitor.

An antibacterial agent preferred for practical clinical use, however, is one that alone can demonstrate antibacterial activity. Furthermore, the DHP inhibitor to be combined with the antibiotic could exert undesirable actions on tissues of the living body. For these reasons, a combined use should be avoided wherever possible. Thus there has been a growing demand for a carbapenem compound having sufficiently high degrees of both antibacterial activity and resistance to DHP.

Recently, there were proposed some carbapenem compounds of the type that could achieve the above objectives. Such carbapenem compounds are 1-methyl-carbapenem compounds in which a methyl group is introduced at the 1-position and various heterocyclyl-thio groups at the 2-position of the carbapenem skeleton. For example, Japanese Laid-Open Patent Publication No. 202,866/1985 to Sankyo discloses 2-heterocyclyl-thio-1-methylcarbapenem compounds including a compound having at the 2-position a (N-methylacetoimidoyl-azetidin-3-yl)thio substituent, represented by the formula (D):

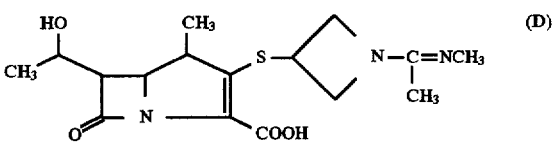

It is reported that this compound has superior antibacterial activities as well as a remarkably improved resistance to decomposition by DHP leading to inactivation so that it demonstrates highly useful effects; however, the Japanese Patent document does not provide any specific antibacterial data or working examples. Therefore, Sankyo does not disclose anything about carbapenem compounds having at the 2-position 1-(1,3-thiazolin-2-yl)azetidin-3-yl-thio substituent according to the present invention. Most recently, International Patent Publication Number WO 93/23,402 to Fujisawa disclosed 2-(3-azetidinylthio) carbapenem compounds represented by the following formula (E):

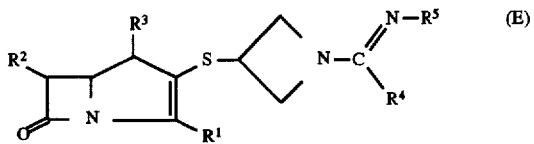

The Fujisawa patent publication has a general disclosure of compounds of the formula (F):

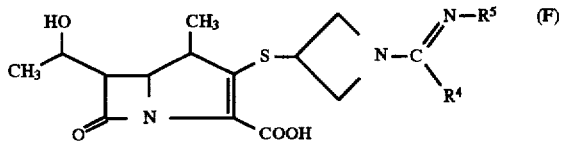

wherein $R^4$ and $R^5$ are combined together to form optionally substituted imino-containing heterocyclic group.

Christensen et al. European published application 0 161 541 is also cited to show the state of the art.

Carbapenem compounds possess a potent antibacterial activity with a broad spectrum. However, like other β-lactam antibacterial agents used in clinical practice, it is anticipated that carbapenem compounds will be uneffective against carbapenem-resistant bacteria. Accordingly, there have been proposed some carbapenem compounds having unique substituents at 2-position of the carbapenem skeleton. Furthermore, even though oral formulations of carbapenem compounds are useful for daily administration, the carbapenem antibiotics which have been proposed in prior patent application are mainly used for injectable formulation. Therefore, there has been a demand for orally administrable carbapenem antibiotics.

SUMMARY OF THE INVENTION

The present invention provides carbapenem compounds having high antibacterial activities, a strong action of inhibiting β-lactamase as well as improved resistance to kidney dehydropeptidase. More specifically, the present invention provides the carbapenem compounds substituted by a methyl group at the 1-position in the β-configuration, in which particularly a [1-(1,3-thiazolin-2-yl)azetidin-3-yl]thio group is introduced at the 2-position.

Accordingly, one object of the present invention is to provide (1R,5S,6S)-2-[1-(1,3-thiazolin-2-yl)azetidin-3-yl]thio-6-[(R)-1-hydroxyethyl]-1-methyl-carbapen-2-em-3-carboxylic acid derivative represented by the following formula:

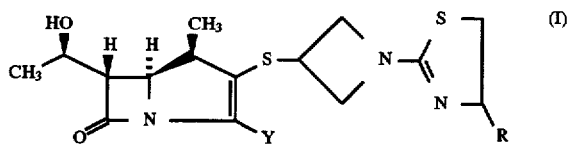

wherein R is hydrogen; lower alkyl group which is unsubstituted or substituted by hydroxy, lower alkoxy which is unsubstituted or substituted by lower alkoxy —COOR$^1$ (R$^1$ is hydrogen or lower alkyl group); or —CONR$^2$R$^3$ (R$^2$ and R$^3$ are, independently of each other, hydrogen or lower alkyl), Y is carboxy, or protected carboxy, or a pharmaceutically acceptable salt thereof.

More specifically, the present invention provides (1R,5S,6S)-2-[1-(1,3-thiazolin-2-yl)azetidin-3-yl]thio-6-[(R)-1-hydroxyethyl]-1-methyl-carbapen-2-em-3-carboxylic acid of the following formula:

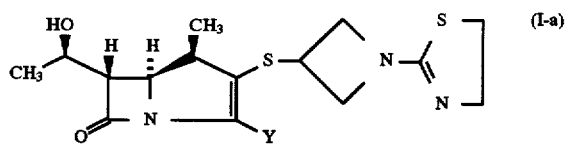

wherein Y has the same meaning as above, or a pharmaceutically acceptable salt thereof.

Still more specifically, the present invention provides (1R,5S,6S)-2-[1-(1,3-thiazolin-2-yl)azetidin-3-yl]thio-6-[(R)-1-hydroxyethyl]-1-methyl-carbapen-2-em-3-carboxylic acid of the following formula:

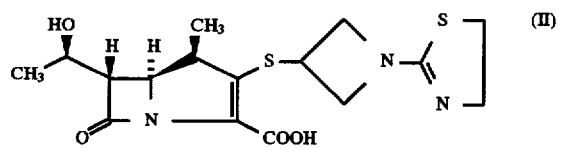

or a pharmaceutically acceptable salt thereof.

Another object of the present invention is to provide orally administrable carbapenem compounds which are converted into active carbapenem compounds of formula (II) in the body and show potent activities against a number of pathogenic microorganisms. For the above purpose of the invention, provided is (1R,5S,6S)-2-[1-(1,3-thiazolin-2-yl)azetidin-3-yl]thio-6-[(R)-1-hydroxyethyl]-1-methyl-carbapen-2-em-3-carboxy late of the following formula:

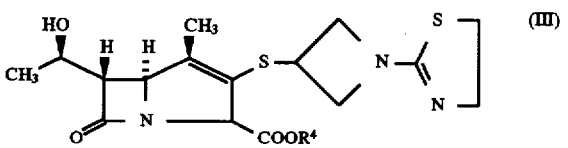

wherein R$^4$ is ester moiety of an esterified carboxy, or a pharmaceutically acceptable salt thereof.

Preferable orally administrable carbapenem compound of the present invention is 1-[(cyclohexyloxy)carbonyloxy]ethyl (1R,5S,6S)-2-[1-(1,3-thiazolin-2-yl)azetidin-3-yl]thio-6-[(R)-1-hydroxyethyl]-1-methyl-carbapen-2-em-3-carboxylate of the following formula:

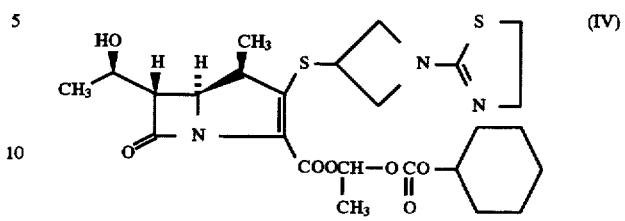

or a pharmaceutically acceptable salt thereof.

The other object of the present invention is to provide antibacterial compositions containing the carbapenem compounds represented by formula (I) or pharmaceutically acceptable salts thereof, as an active ingredient.

Preferable antibacterial composition is orally-administrable formulation containing the carbapenem compound of formula (IV).

DETAILED DESCRIPTION OF THE INVENTION

The carbapenem compounds according to the present invention are novel compounds that are not specifically disclosed in the prior patent publications (for instance, Japanese Patent Laid-Open Publication No. 202,836/1985, and WO 93/23,402). In particular, they are remarkably characterized in that the substituent at the 2-position of the carbapenem skeleton is a [1-(1,3-thiazolin-2-yl)azetidin-3-yl]thio group and in that they have superior antibacterial activities and resistance to DHP.

In the specification of the present application, the term "lower" qualifying a group of a compound means that the group or compound so qualified has from 1 to 7, preferably from 1 to 4, carbon atoms.

The term "alkyl" referred to herein stands for a straight-chained or branched-chain hydrocarbon group having preferably from 1 to 20 carbon atoms and may include, for example, methyl, ethyl, n-propyl, isopropyl, n-butyl, isobutyl, sec-butyl, tert.-butyl, n-pentyl, isopentyl, n-hexyl, isohexyl, n-heptyl, isoheptyl, octyl, isooctyl, monanyl, dodecanyl, pentadecanyl, eicosanyl or the like.

The term "alkoxy" referred to herein stands for an alkyloxy group in which the "alkyl" group has the meaning as mentioned above. Examples include methoxy, ethoxy, n-propoxy, isopropoxy, n-butoxy, isobutoxy, sec-butoxy, tert-butoxy, n-pentyloxy, isopentyloxy, n-hexyloxy, isohexyloxy, n-heptyloxy, isoheptyloxy or the like. Among them, methoxy, ethoxy, isobutoxy, sec-butoxy or tert-butoxy is preferably used.

The term "protected carboxy" is esterified carboxy which is represented by the group —COOR$^4$ (wherein R$^4$ is ester moiety of an esterified carboxy). Suitable ester moiety of an esterified carboxy represented by the group "R$^4$" is lower alkyl which may have at least one suitable substituent(s), and can be represented by the following group:

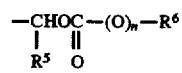

wherein R$^5$ is hydrogen or alkyl group,

R$^6$ is alkyl or cycloalkyl group in which these groups may be substituted by alkoxy, group: —OP(=O)(OR$^7$) (wherein R$^7$ is hydrogen, alkyl, aryl or aralkyl), carboxyl or propylglycinamide; and n is 0 or 1.

The term "aryl" may be monocyclic or polycyclic aryl group which may have at least one substituent(s) such as alkyl, for example, phenyl, tolyl, xylyl, α-naphthyl or β-naphthyl and the like.

Suitable "aralkyl" may include aryl substituted alkyl in which the "aryl" group and "alkyl" group have the meanings as mentioned above. Examples include benzyl, benzhydryl, trityl, phenethyl, α-methylbenzyl, phenylpropyl, naphthylmethyl and the like.

The term "cycloalkyl" may be saturated monocyclic hydrocarbon group having from 3 to 7 ring carbon atoms, and for example cyclopropyl, cyclobutyl, cyclopentyl, cyclohexyl, cycloheptyl or the like.

Therefore, suitable "ester moiety" is for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1-(or 2-)acetoxyethyl ester, 1-(or 2- or 3-)acetoxypropyl ester, or 1-(or 2- or 3- or 4-)acetoxybutyl ester, 1-(or 2-)propionyloxyethyl ester, 1-(or 2- or 3-)propionyloxypropyl ester, 1-(or 2-)butyryloxyethyl ester, 1-(or 2-)isobutyryloxyethyl ester, 1-(or 2-)pyvaloyloxyethyl ester, 1-(or 2-)hexanoyloxyethyl ester, isobutyryloxymethyl ester, 2-ethylbutyryloxymethyl ester, 3,3-dimethylbutyryloxymethyl ester, 1-(or 2-)pentanoyloxyethyl ester, etc.], lower alkanesulfonyl (lower)alkyl ester (e.g. 2-mesylethyl ester, etc.), mono(or di or tri)halo(lower)alkyl ester (e.g. 2-iodoethyl ester, 2,2,2-trichloroethyl ester, etc.); lower alkoxycarbonyloxy(lower) alkyl ester [e.g. methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-)isopropoxycarbonyloxyethyl ester, etc.], cycloalkyloxycarbonyloxy(lower)alkyl ester (e.g. cyclohexyloxycarbonyloxymethyl ester, 1-(or 2-)cyclohexyloxycarbonyloxy ethyl ester, etc.), phthalidylidene(lower)alkyl ester, or (5-lower alkyl-2-oxo-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl) methyl ester, (5-propyl-2-oxo-1,3-dioxol-4-yl)ethyl ester, etc.]; or the like. More preferable example of the protected carboxy thus defined may be pivaloyloxymethyloxycarbonyl or 1-(cyclohexyloxycarbonyl)ethyloxycarbonyl.

Typical examples of the compounds of formula (I) are shown in the following Table 1 and Table 2.

TABLE 1

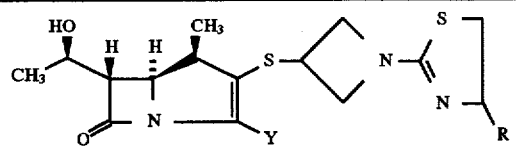

| R | Y |
|---|---|
| H | COOH |
| CH₃ | COOH |
| CH(CH₃)₂ | COOH |
| CH₂OH | COOH |
| CH₂OCH₂CH₃ | COOH |
| CH₂OCH₂OCH₃ | COOH |
| COOC₂H₅ | COOH |
| CON(CH₃)₂ | COOH |

TABLE 2

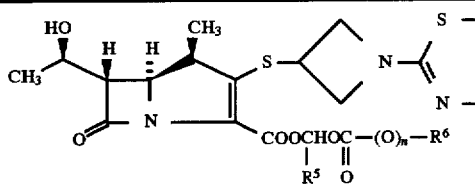

| $R^5$ | $\underset{O}{\overset{\parallel}{OC}}-(O)_n-R^6$ |
|---|---|
| H | OCCH₃ ‖ O |
| CH₃ | OCCH₃ ‖ O |
| C(CH₃)₃ | OCCH₃ ‖ O |
| H | OCCH₂OCH₃ ‖ O |
| CH₃ | OCCH₂OCH(CH₃)₂ ‖ O |
| H | OC—⟨cyclohexyl⟩ ‖ O |
| (CH₂)₅CH₃ | OC—⟨C₆H₁₀—H⟩ ‖ O |
| H | OC—⟨C₆H₃(H)(OCH₃)⟩ ‖ O |
| H | OCC(CH₃)₃ ‖ C |
| C(CH₃)₃ | OCC(CH₃)₃ ‖ C |
| H | OCC₄H₉ ‖ C |
| H | OCC₇H₁₅ ‖ C |
| CH₃ | OCC₇H₁₅ ‖ C |
| H | OCC₁₅H₃₁ ‖ C |
| CH₃ | OCC₁₅H₃₁ ‖ C |
| H | OCCH₂CH₂OP(OH)₂ with O above and below |

TABLE 2-continued

[Structure: carbapenem core with HO-CH(CH₃)-, CH₃, S-azetidine-N=C(S)-N (thiourea), COOCH(R⁵)OC(=O)-(O)ₙ-R⁶]

$$\begin{array}{c} \text{OC}-(\text{O})_n-\text{R}^6 \\ \parallel \\ \text{O} \end{array}$$

| R⁵ | |
|---|---|
| H | OCCH₂CHOP(OC₆H₅)₂ with ‖O and CH₃ |
| H | OC-cyclohexyl-OP(OH)₂ (‖O on carbonyl, ‖O on P) |
| H | OC-cyclohexyl-OP(OC₆H₅)₂ (‖O on carbonyl, ‖O on P) |
| H | OC(CH₂)₃COOH (‖O) |
| CH₃ | OC(CH₂)₃COOH (‖O) |
| H | OC-cyclohexyl-COOH (‖O) |
| H | OC(CH₂)₇COOH (‖O) |
| CH₃ | OC(CH₂)₇COOH (‖O) |
| H | OC(CH₂)₅OP(OH)₂ (‖O, ‖O) |
| CH₃ | OC(CH₂)₅OP(OH)₂ (‖O, ‖O) |
| H | OC(CH₂)₃CNHCH₂C—N-pyrrolidine-COOH (‖O, ‖O, ‖O) |
| CH₃ | OC(CH₂)₇CNHCH₂C—N-pyrrolidine-COOH (‖O, ‖O, ‖O) |

TABLE 2-continued

[Same carbapenem structure as above]

| R⁵ | |
|---|---|
| H | OCOCH₃ (‖O) |
| H | OCO(CH₂)₃OCH₃ (‖O) |
| H | OCOCH₂CH₂OP(OCH₃)₂ (‖O, ‖O) |
| H | OCO-cyclohexyl (‖O) |
| CH₃ | OCO-cyclohexyl (‖O) |
| H | OCOC(CH₃)₃ (‖O) |
| CH₃ | OCOC₄H₉ (‖O) |
| H | OCOC₁₅H₃₁ (‖O) |
| H | OCO(CH₂)₃COOH (‖O) |
| H | OCO-cyclohexyl-OP(OCH₃)₂ (‖O, ‖O) |

The pharmaceutically acceptable salts of the above listed compounds are also included in the examples of the compounds of the present invention.

Furthermore, when the compounds of the present invention have an asymmetric carbon in the side chain at the 2-position or 3-position, these optically active compounds can be stereo-selectively obtained by using the optically active starting materials (see the examples described below), or they can be also obtained by resolution of the diastereoisomeric mixture of these compounds by ordinary methods. Therefore, the optically active and stereoisomeric mixture of the compounds (I) should be included in the compounds of the present invention.

The compounds of the present invention of the formula (I) may be prepared in accordance with the processes as illustrated by the reaction schemes shown below.

The compound of formula (I) in which the group "Y" is carboxy or —COO⁻ may be prepared by the following Reaction Scheme A:

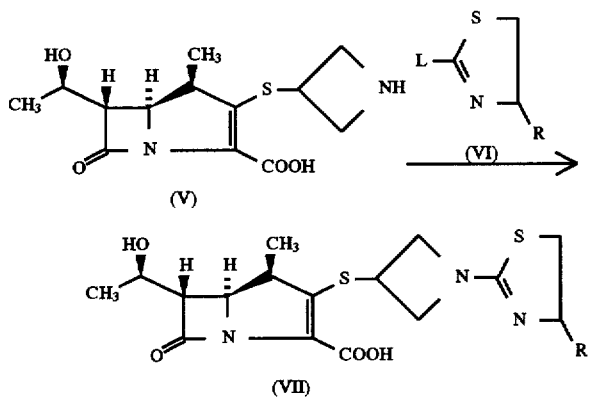

wherein L is a leaving group; and R has the same meaning as above.

mately 1 to approximately 10 moles, preferably in a range from approximately 1 to approximately 5 moles, per mole of the compound of formula (V). If necessary, an organic solvent, alcohol such as methanol, ethanol or isopropanol; ether such as diethyl ether or tetrahydrofuran; acetonitrtle; dimethylformamide; or dimethylacetamide can be used as the reaction solvent together with the above buffer solution. The reaction temperature is not limited to a particular range and many vary in a wide range according to the starting material of (VI) to be used. It may range generally from about −78° C. to about 50° C. preferably from about −20° C. to about 0° C. The reaction may be finished in approximately 5 minutes to approximately 5 hours.

The compounds of formula (V) to be employed as a starting compound in the above reaction are known compounds or may be prepared in accordance with the known method described in Japanese Patent Publication No. 255, 280/1988.

Furthermore, the compound of the present invention of the formula (I) in which the group "Y'" is carboxy or —COO⁻ may also be prepared in accordance with the following Reaction Scheme B.

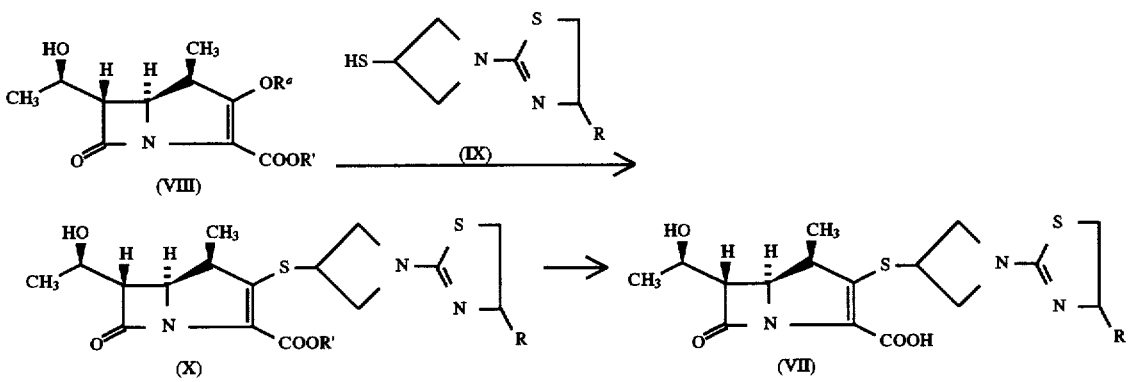

The "leaving group" represented by L in the formula (VI) may, for example, be an azido group; a halogen atom such as chlorine, bromine or fluorine; lower alkanoyloxy group such as acetoxy or propionyloxy; sulfonyloxy group such as benzenesulfonyloxy, tosyloxy or methanesulfonyloxy; lower alkoxy group such as methoxy or ethoxy; lower alkylthio group such as methylthio or ethylthio.

The reaction of (1R,5S,6S)-2-[(azetidin-3-yl)]thio-6-[(R)-1-hydroxyethyl]-1-methyl-carbapen-2-em-3-carboxylic acid of formula (V) with the compound of formula (VI) may be carried out, for instance, by reacting the compound of formula (V) with the compound (VI) in an appropriate buffer-solvent of pH 5 to 7 such as a phosphate buffer solution, an acetate buffer solution, a citrate buffer solution, a morpholino-propane sulfonate buffer solution, an N-methylmorpholino phosphate buffer solution or the like. The reaction can be carried out by adding the compound of formula (VI) into the solution mixture of the compound of formula (V) and by stirring the reaction mixture for an appropriate time.

The quantity of the compound of formula (VI) is not critical and may vary appropriately in a range from approxiwherein $R^a$ is an acyl group; R' is a carboxyl protecting group; and R has the same meaning as above.

The term "acyl group" represented by $R^a$ may be, in a narrower sense, a moiety obtainable by removing the hydroxyl group from the carboxyl group of an organic carboxylic acid as well as, in a broader sense, any acyl group derived from an organic sulfonic acid or an organic phosphoric acid. Such an acyl group may include, for example, a lower alkanoyl group such as acetyl, propionyl, butyryl or the like, a (halo)lower alkyl sulfonyl group such as methanesulfonyl, trifluoromethanesulfonyl or the like; a substituted or unsubstituted arylsulfonyl group such as benzenesulfonyl, p-nitrobenzenesulfonyl, p-bromobenzenesulfonyl, toluenesulfonyl, 2,4,6-triisopropylbenzenesulfonyl or the like; and diphenylphosphoryl.

The term "carboxyl protecting group" represented by R' stands for any group capable of protecting the carboxyl group of the compound involved without adversely affecting any other substituents and the reactions that follow and may include, for example, an ester residue such as a lower alkyl ester residue including, for example, methyl ester, ethyl ester, n-propyl ester, isopropyl ester, n-, iso-, sec- or tert.-butyl ester, n-hexyl ester or the like; an aralkyl ester residue including, for example, benzyl ester, n-nitrobenzyl ester, o-nitrobenzyl ester, p-methoxybenzyl ester or the like; and a lower aliphatic acyloxymethyl ester residue including, for example, acetoxymethyl ester, propionyloxymethyl ester, n- or iso-butyryloxymethyl ester, pivaloxyloxymethyl ester or the like.

The reaction of the compound of formula (VIII) with [1-(1,3-thiazolin-2-yl)azetidin-3-yl]thiol of the formula (IX) may be carried out, for instance, by reacting the compound of formula (VIII) with the compound of formula (IX) in an amount ranging from approximately 0.5 molar to approximately 5 molar, preferably from approximately 0.8 molar to approximately 3 molar amount in an appropriate solvent such as tetrahydrofuran, dichloromethane, dioxane, dimethylformamide, dimethylsulfoxide; acetonitrile, hexamethylene phosphoramide or the like, preferable in the presence of a base such as sodium hydrogen carbonate, potassium carbonate, triethylamine, diisopropylethyl amine or the like at a temperature ranging from approximately −40° C. to approximately 25° C. for approximately 30 minutes to approximately 24 hours.

Preferably, the reaction may be carried out in an inert atmosphere, for example in an atmosphere of nitrogen gas or argon gas.

The reaction described above provides the compound of formula (X), and the resulting reaction mixture containing the compound of formula (X) may be used for the next reaction without further purification; or the compound (X) may be isolated from the reaction mixture by ordinary methods, if necessary.

In the reaction of the compound of formula (VIII) with the compound of formula (IX), another compound (IX') wherein the mercapto group of the formula (IX) is protected by a merecapto-protecting group may be used instead of the compound (IX). The reaction may be carried out in the following manner: the mercapto-protecting group of the compound (IX) is removed by ordinary methods used in the amino acid chemistry, then, without isolating the resulting compound (IX), to the reaction mixture the compound of formula (VIII) is added. The reaction condition is the same as above.

The carbapenem compounds of the present invention of the formula (VII) may be obtained by removal of the carboxyl protecting group R' of the compounds of the formula (X) obtained by the reaction method described above. The removal of the protecting group R' may be made by a reaction known per se for removing a protective group, such as solvolysis or hydrogenolysis. In a typical reaction, the compound represented by formula (X) may be treated, for instance, in a mixture of solvents such as tetrahydrofuran-water, tetrahydrofuran-ethanol-water, dioxane-water, dioxane-ethanol-water, n-butanol-water or the like containing a acetate buffer solution (pH 5.5), morpholino-propane sulfonic acid-sodium hydroxide buffer solution (pH 5.5), a phosphate buffer solution (pH 5.5), dipotassium phosphate, sodium bicarbonate or the like, using hydrogen under 1 to 4 atmospheric pressures, in the presence of a catalyst for hydrogenation such as platinum oxide, palladium-activated carbon or palladium hydroxide-activated carbon at temperatures ranging from approximately 0° C. to approximately 50° C. for approximately 0.25 to approximately 5 hours.

Furthermore, the removal of the protecting group R' of the compound of formula (X) may also be carried out by reacting the compound (X) with zinc in a buffer. In a typical reaction, the compound of formula (X) may be treated with zinc in an appropriate buffer solvent of pH 5 to 7 such as a phosphate buffer solution, an acetate buffer solution, a citrate buffer solution, a morphorinopropanesulfonate buffer solution, or an N-methylmorphorine buffer solution. Zinc used in the reaction may include, for example, elemental zinc in the form of powder, flower or granule or the like.

The amount of zinc used in this reaction is not strictly limited; however, in general, it is conveniently about 1 to 10 parts by weight, preferably 1 to 5 parts by weight per part by weight of the compound of formula (X) to be reacted.

In this reaction, an organic solvent may be used in combination. Examples of the solvent are alcohols such as ethanol, propanol and n-butanol; ethers such as diethyl ether and tetrahydrofuran; acetonitrile, dimethylformamide and dimethylacetamide. Usually, the reaction may be finished in approximately 5 minutes to approximately 5 hours in a reaction temperature from about −20° C. to about 50° C., preferably from the room temperature to about 30° C.

The compound of formula (VIII) to be employed as a starting compound in the above reaction is known per se and may be prepared in such a manner as disclosed, for example, in Japanese Laid-Open Patent Publication No. 123,985/1981 or, more preferably, in accordance with the stereo-selectivity method as disclosed in Japanese Laid-Open Patent Publication No. 284,176/1988.

Furthermore, [1-(1,3-thiazolin-2-yl)azetidin-3-yl]thiol of the formula (IX) may be prepared in accordance with the method described in the synthetic examples or working examples mentioned later, or may be easily prepared from commercially available compounds.

As a result, (1R,5S,6S)-2-[1-(1,3-thiazolin-2-yl)azetidin-3-yl]thio-6-[(R)-1-hydroxyethyl]-1-methyl-carbapen-2-em-3-carboxylic acids represented by formula (I) in which "Y" is carboxy are produced in extremely high yield. These compounds may be isolated by using ion-exchange resins or polymer resins.

The present invention provides orally administrable ester derivatives of carbapenem compounds, that is, (1R,5S,6S)-2-[1-(1,3-thiazolin-2-yl)azetidin-3-yl]thio-6-[(R)-1-hydroxyethyl]-1-methyl-carbapen-2-em-3-carboxylates of formula (I) in which the group "Y" is protective carboxy. The ester derivatives of the present invention of the formula (I) may be prepared in accordance with the following Reaction Scheme C:

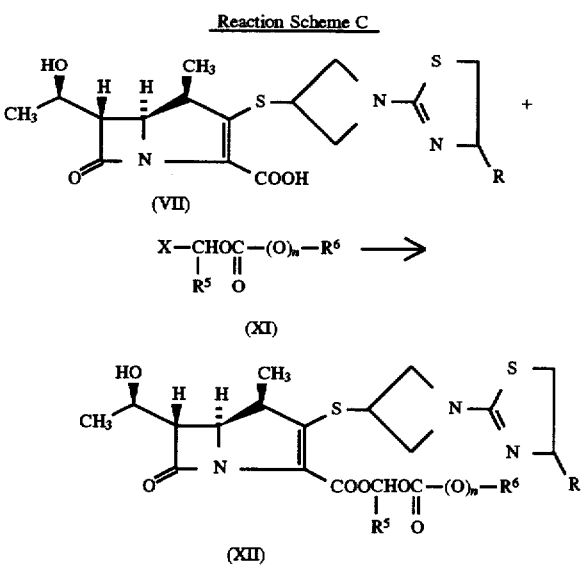

wherein X is halogen; and R, R$^5$, R$^6$ and n have the same meanings as above.

In the Reaction Scheme C, halogen represented by X may be chlorine, iodine, bromine or fluorine.

The reaction of (1R,5S,6S)-[1-(1,3-thiazolin-2-yl)azetidin-3-yl]thio-6-[(R)-1-hydroxyethyl]-1-methylcarbapen-2-em-3-carboxylic acid of formula (VII) with the compound of formula (XI) may be carried out, for instance, first by obtaining an alkali metal salt of formula (VII) in water by reacting the compound of formula (VII) with an appropriate alkali metal bases such as sodium hydroxide, potassium hydroxide, sodium carbonate, potassium carbonate, sodium bicarbonate, potassium bicarbonate or the like. Then, the alkali metal salt of formula (VII) thus obtained is reacted with the compound of formula (XI) in inert organic solvent, for example, ethers such as diethyl ether, tetrahydrofuran, dioxane; carbon hydrides such as benzene, toluene, xylene, cyclohexane; N,N-dimethylformamide, dimethylsulfoxide, acetonitrile, preferably in dimethylformamide under stirring.

The quantity of the alkali metal base is not critical and may vary appropriately in a range from approximately 1 to approximately 10 moles, preferably in a range from approximately 1 to approximately 5 moles, per mole of the compound (VII). The reaction temperature is not limited to a particular range and may vary from about 0° C. to room temperature. The reaction may be finished in approximately 2 or 3 minutes to approximately 1 hour under these conditions.

Furthermore, the quantity of the compound of formula (XI) is not critical and may vary appropriately in a range from approximately 1 to approximately 3 moles, preferably in a range from approximately 1 mole to approximately 1.5 moles, per mole of the alkali metal salt of formula (VII). The reaction temperature is not limited and generally may vary in a range from about −20° C. to about 50° C., preferably in a range from 0° C. to room temperature, and the reaction may be finished in approximately 10 minutes to approximately 2–3 hours.

Thus, (1R,5S,6S)-2-[1-(1,3-thiazolin-2-yl)azetidin-3-yl]thio-6-[(R)-1-hydroxyethyl]-1-methyl-carbapen-2-em-3-carboxylates represented by the formula (I) in which Y is protected carboxy [compounds of formula (XII)] are produced and these compounds may be isolated and purified by usual method, for example, filtration, decantation, extraction, washing, removal of the solvent, column chromatography, thin-layer chromatography, recrystalization, distillation, sublimation or the like.

The compounds of formula (VII) to be employed as a starting compound in the above Reaction Scheme C can be prepared in accordance with the method described in the examples mentioned later.

The compounds of the present invention represented by formula (I) may be converted to a pharmaceutically acceptable acid addition salt thereof with inorganic or organic acids; these include, for example, aliphatic acid such as acetic acid, propionic acid, butyric acid, trifluoroacetic acid, trichloroacetic acid or the like; substituted or unsubstituted benzoic acid such as benzoic acid, p-nitrobenzoic acid or the like; lower-(halo)alkylsulfonic acid such as methanesulfonic acid, trifluoromethanesulfonic acid or the like; substituted or unsubstituted arylsulfonic acid such as benzensulfonic acid, p-nitro benzenesulfonic acid, p-bromobenzenesulfonic acid, toluenesulfonic acid, 2,4,6-triisopropylbenzensulfonic acid or the like; organic phosphinic acid such as diphenylphosphinic acid; and inorganic acid such as hydrochloric acid, sulfuric acid, hydrobromic acid, hydriodic acid, borofluoric acid, nitrous acid or the like.

The desired compounds of formula (I) in accordance with the present invention are novel compounds that are not disclosed specifically in the above-mentioned publication and that are extremely stable against dehydropeptidase (DHP) known as a kidney enzyme and have superior antibacterial activities. Furthermore, the orally administrable carbapenem compounds of the present invention show good intestinal absorption in the body and easily converted to active carbapenem compound which is highly active against a number of pathogenic microorganisms. Therefore, the carbapenem compounds of the present invention of formula (I) in which the group Y is protective carboxy may be used as pro-drug type antibiotics for oral administration and are useful for practical clinical use. The remarkably high antibacterial activities, intestinal absorption and stability against the kidney DHP of the compounds of formula (I) according to the present invention have been determined by biological tests described below.

I. Antibacterial Tests

Test Procedures:

The antibacterial activities were tested by an agar plate dilution method in accordance with the standard method of The Japanese Chemotherapy Society [Chemotherapy, Vol. 29, 76–79 (1981)].

A Mueller-Hinton (MH) agar liquid medium of a test microorganism was cultured overnight at 37° C. and the resultant culture medium was diluted with a buffered saline gelatin (BSG) solution to contain approximately $10^6$ cells of the test microorganisms per milliliter, and then the diluted solution was inoculated with a microplanter at the rate of approximately 5 microliters on a MH agar medium containing a test compound. This medium was then incubated at 37° C. for 18 hours. The minimum inhibitory concentration (MIC) is determined as a minimum concentration in which no test microorganism could grow. It is noted here that the test organisms used were all standard strains.

Results:

Table 3 shows the test results. The test compounds used therein were the Compound (28) obtained in Example 2, which is the active compound of the Compound (33) obtained in Example 6, and the Compound (31) obtained in Example 4.

TABLE 3

MINIMUM INHIBITORY CONCENTRATIONS (MIC)

| | MIC (µg/ml) Test Compounds | |
|---|---|---|
| Test Organisms | (28) | (31) |
| S. aureus FDA209P JC-1 | 0.013 | 0.05 |
| S. aureus Terajima | ≦0.006 | ≦0.006 |
| S. aureus MS353 | ≦0.006 | 0.025 |
| S. pyogenes Cook | ≦0.006 | ≦0.006 |
| B. subtilis ATCC 6633 | 0.025 | 0.025 |
| M. luteus ATCC 9341 | 0.2 | 0.2 |
| E. coli NIHJ JC-2 | 0.013 | 0.05 |
| E. coli K-12 C600 | 0.1 | 0.2 |
| E. cloacae 963 | 0.05 | 0.2 |
| E. aerogenes ATCC 13048 | 0.1 | 0.39 |
| K. pneumoniae PCI-602 | 0.013 | 0.013 |
| S. typhimurium 11D971 | 0.025 | 0.1 |
| S. typhi 901 | ≦0.006 | 0.05 |
| S. paratyphi 1015 | 0.05 | 0.05 |
| S. schottmuelleri 8006 | 0.025 | 0.2 |
| S. enteritidis G14 | 0.39 | 0.2 |
| S. marcescens IAM 1184 | 0.05 | 0.39 |
| M. morganii IFO 3848 | 0.39 | 0.2 |
| P. mirabilis IFO 3849 | 0.39 | 0.78 |
| P. vulgaris OX-19 | 0.1 | 0.1 |
| P. vulgaris HX-19 | 0.1 | 0.39 |

TABLE 3-continued

MINIMUM INHIBITORY CONCENTRATIONS (MIC)

| Test Organisms | MIC (μg/ml) Test Compounds | |
|---|---|---|
| | (28) | (31) |
| P. rettgeri IFO 3850 | 0.39 | 6.25 |

The foregoing results clearly demonstrate that the carbapenem compounds according to the present invention have superior antibacterial activities against Staphylococcus, Streptococcus, Klebsiella and Proteus.

II. Antibacterial Activities against Clinically Isolated Microorganism

Test Procedures:

1. Strains of Test organisms

The following strains clinically isolated freshly in Japan were used in this test.

| MRSA | 28 strains |
|---|---|
| S. epidermidis | 23 strains |
| E. faecalis | 16 strains |
| E. coli | 20 strains |
| E. cloacae | 14 strains |
| K. pneumoniae | 23 strains |
| S. marcescens | 27 strains |

2. The test was carried out by the agar plate dilution method in accordance with the standard method of The Japanese Chemotherapy Society. The minimum inhibitory concentration (MIC) was determined in substantially the same manner as the test procedures described in Test I.

Results:

The Compound (28) obtained in Example 2 was used in this test. The control compounds used were ceftazidime (CAZ) as a cephalosporin compound, and imipenem as a carbapenem compound, which are widely used in clinical practice.

Table 4 shows the test results. In the table, 50% inhibitory concentrations $MIC_{50}$ against test strains are listed.

TABLE 4

$MIC_{50}$ against CLINICALLY ISOLATED MICROORGANISM (μg/ml)

| | Test Species | | |
|---|---|---|---|
| Test Compounds | MRSA | S. epidermidis | E. faecalis |
| Compound (28) | 0.78 | 0.39 | 0.39 |
| Imipenem | 3.13 | 0.2 | 0.78 |
| CAZ | 100 | 12.5 | 25 |

| | Test Species | | |
|---|---|---|---|
| Test Compounds | E. coli* | E. cloacae | K. pneumoniae |
| Compound (28) | 0.05 | 0.1 | 0.025 |
| Imipenem | 0.78 | 0.2 | 0.2 |
| CAZ | 3.13 | 1.56 | 0.2 |

| | Test species |
|---|---|
| Test Compound | S. marcescens |

TABLE 4-continued $MIC_{50}$ against CLINICALLY ISOLATED MICROORGANISM (μg/ml)

| Compound (28) | 0.2 |
|---|---|
| Imipenem | 1.56 |
| CAZ | 0.39 |

*In the case of E. coli, $MIC_{100}$ data are shown.

The foregoing results clearly demonstrate that the carbapenem compounds according to the present invention have superior antibacterial activities.

III. Stability Test against Renal Dehydropeptidase-1

Test Procedures:

The stability of the carbapenem compounds of the present invention was measured with a purified enzyme extracted from the swine kidney cortex. As a substrate, the compound was adjusted to give a final concentration of 35 μg/ml and was then added to the enzyme solution in 50 mM MOPS buffer (pH 7.0). The reaction mixture was incubated at 30° C. for 2 hours and then diluted with an equal volume of methanol. The residual antibiotic activity in the supernatant after centrifugation at 1000×g for 20 minutes was determined by a bioassay method by using Staphylococcus aureus Terajima. Standard curves were calculated by using inactivated enzyme as a control.

Compound (28) obtained in Example 2 below was used as a test compound and imipenem was used as a control compound.

Results:

Table 5 below shows the results of the stability test of the compound according to the present invention and imipenem against swine renal dehydropeptidase-1.

TABLE 5

STABILITY TO SWINE RENAL DHP-1

| Test Compounds | 0 | 30 | 60 | 120 | 240 (min) |
|---|---|---|---|---|---|
| Compound (28) | 100 | 100 | 82.9 | 67.1 | 40.0 |
| Imipenem | 100 | 35 | 10 | 3 | 0 |

*Residual activity (%)

The stability test results against DHP-1 clearly show that the carbapenem compound according to the present invention was more stable than imipenem.

IV. In Situ Experiments on Absorption from Rat Intestinal Loop

Method:

7-week-old male rats of Wistar strain were used after fasting overnight. After anesthetizing the animals with ether, the intestine was exteriorized and an acute loop of 30 cm length was prepared from the upper part of jejunum by ligature of both ends. 0.2% physiological saline solutions of the test compounds were injected at a dose of 20 mg/kg into the loop with a syringe, and the loop was returned. About 0.4 ml blood was taken from the vena juguiaris at 10, 30, 60 and 120 minutes after dosing. Then the plasma concentrations of the test compounds or the active metabolite were measured by HPLC. And the area under the plasma concentration level-time curve (AUC) for 2 hours after administration was calculated.

As the test compounds, the Compounds (28), (32) and (33) obtained in the Examples 2, 5 and 6, respectively, were used.

Results:

Table 6 shows the test results. In the table, the maximum concentrations of the test compounds in plasma (C max) and the AUCs (μg.hr/ml) are shown. After administration of the Compounds (32) and (33), these compounds were undetectable and the deesterified active compound [Compound (28)] was only detected. Therefore, in the cases of these compounds, the test results are shown as those of Compound (28).

TABLE 6

INTESTINAL ABSORPTION

| Test Items | Test Compounds | | |
|---|---|---|---|
| | (28) | (32) | (33) |
| C max (μg/ml) | 0.8 | 8.4 | 12.3 |
| AUC (μg · hr/ml)(0-2 hr) | 1.0 | 9.4 | 15.7 |

The foregoing results clearly show that the orally administrable carbapenem compounds of the present invention have superior intestinal absorption. That is, after administration of Compounds (32) and (33), these compounds were easily absorbed in the body and then quickly converted to the active carbapenem compound [Compound (28)].

V. Oral Absorption Study
Method:

5-week-old male mice of ddY strain were used after fasting overnight. The test compounds in 1% physiological saline solution at a dose of 100 mg/kg were administered orally to a group of 2 mice. Blood was taken from the vena jugularis at 15, 30, 60 and 120 minutes after dosing. Then the concentrations of the test compounds or the active metabolite and the area under the plasma concentration level-time curve (AUC) were calculated in the same way mentioned above.

As the test compounds, the Compounds (28), (32) and (33) of the present invention obtained in the Examples 2, 5 and 6 were used.

Results:

Table 7 shows the test results. In the table, the maximum concentrations of the test compounds in plasma (C max) and the AUCs (μg.hr/ml) are shown. After administration of the Compounds (32) and (33), these compounds were undetectable and the deesterified active compound [Compound (28)] was only detected. Therefore, in the cases of these compounds, the test results are shown as those of Compound (28).

TABLE 7

ORAL ABSORPTION (μg/ml)

| Test Items | Test Compounds | | |
|---|---|---|---|
| | (28) | (32) | (33) |
| C max (μg/ml) | 3.5 | 131.2 | 128.3 |
| AUC (μg · hr/ml) (0-2 hr) | 5.0 | 147.8 | 150.2 |

From the in vivo test results, the orally administrable carbapenem compounds of the present invention showed a good oral absorption.

VI. Toxicity

Toxicological studies were carried out using a group of 10 male mice of CrjCD(SD) strain weighing from 20 to 23 grams. Solutions containing each of the carbapenem Compounds (28), (31), (32) and (33) of the present invention were administered subcutaneously to the mice and subjected to observations for one week.

The results have revealed that the group of mice to which the carbapenem compounds of the present invention had been administered in the amount of 500 mg/kg were alive without any abnormal findings.

As described above, the carbapenem compounds according to the present invention demonstrate a wider scope of antibacterial spectra than do conventional cephalosporin compounds, and remarkable antibacterial activities comparable to imipenem as well as an over-whelmingly higher resistance against DHP than imipenem.

Therefore, the carbapenem compounds of formula (I) according to the present invention permit a single administration without combination with any other compounds and without a risk of any side effect that might be caused in their combined use with a DHP inhibitor, unlike imipenem that was led for the first time to a practically useful antibacterial agent in combination with cilastatin acting as a DHP inhibitor. The carbapenem compounds are accordingly extremely useful as antibacterial agents for therapy and prevention of infectious diseases from various pathogenic organisms.

The carbapenem compound of formula (I) according to the present invention may be administered as an antibacterial agent to the human being and other mammalian animals in the form of a pharmaceutically acceptable composition containing an antibacterially effective amount thereof. The administration dose may vary in a wide range with ages, patients, weights and conditions of patients, forms or routes of administration, physicians' diagnoses or the like and may be orally, parenterally or topically administered, to adult patients usually in a standard daily dose range from approximately 200 to approximately 3,000 mg once or in several installments per day.

The pharmaceutically acceptable composition of the carbapenem compound of formula (I) according to the present invention may contain an inorganic or organic, solid or liquid carrier or diluent, which is conventionally used for preparation of medicines, particularly antibiotic preparations, such as an excipient, e.g., starch, lactose, white sugar, crystalline cellulose, calcium hydrogen phosphate or the like; a binder, e.g., acacia, hydroxypropyl cellulose, alginic acid, gelatin, polyvinyl pyrrolidone or the like; a lubricant, e.g., stearic acid, magnesium stearate, calcium stearate, talc, hydrogenated plant oil or the like; a disintegrator, e.g., modified starch, calcium carboxymethyl cellulose, low substituted hydroxypropyl cellulose or the like; or a dissolution aid, e.g., a non-ionic surface active agent, an anionic surface active agent or the like, and may be prepared into forms suitable for oral, parenteral or topical administration. The formulations for oral administration may include solid preparations such as tablets, coatings, capsules, troches, powders, fine powders, granules, dry syrups or the like or liquid preparations such as syrups or the like; the formulations for parenteral administration may include, for example, injectable solutions, drip-feed solutions, depositories or the like; and the formulations for topical administration may include, for example, ointments, tinctures, creams, gels or the like. These formulations may be formed by procedures known per se to those skilled in the art in the field of pharmaceutical formulations.

The carbapenem compounds of formula (I) according to the present invention are suitably administered in the form of oral or parenteral formulations, particularly in the form of oral formulations.

The production of the carbapenem compounds of the formula (I) according to the present invention will be described more in detail by way of working examples.

In the following description, the following symbols are used to have the particular meanings.

Me: methyl group
Et: ethyl group
Ac: acetyl group
Ph: phenyl group
PNB: p-nitrobenzyl group
PNZ: p-nitrobenzyloxycarbonyl group
i-Pr: isopropyl
t-But: tert.-butyl
Boc: t-butoxycarbonyl
Preparation 1:

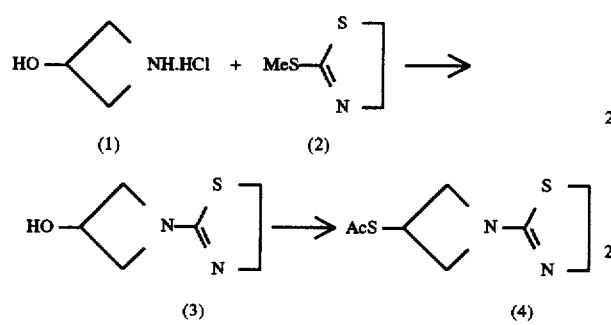

(a) To a solution of 109 mg of 3-hydroxyazetidine. HCl [Compound (1)] in 5 ml of ethanol was added a mixture of 133 mg of 2-methylthiazoline [Compound (2)] and sodium methoxide, and the reaction mixture was refluxed for 8 hours. After removal of the solvent under reduced pressure, the resulting residue was dissolved in chloroform and washed with 50% aqueous potassium carbonate solution. The solvent was removed under reduced pressure to give 119 mg (81.5%) of 3-hydroxy-1-(thiazolin-2-yl)azetidine [Compound (3)] as a crystaline.

$^1$H-NMR(CDCl$_3$) δ:3.356 (t, 2 H, J=7.26 Hz), 3.70–4.00 (m, 4 H), 4.211 (t, 2 H, J=8.21 Hz), 4.622–4.705 (m, 1 H), 4.971 (s, 1 H)

(b) To a mixture solution of triphenylphosphine and diethyl azodicarboxylate in 10 ml of tetrahydrofuran was added a mixture of 119 mg of Compound (3) and thioacetic acid under ice-cooling, and the reaction mixture was stirred for 1 hour at the same condition, then for 1 hour at room temperature. After the reaction solvent was removed under reduced pressure, the resulting residue was purified by silica gel column chromatography (chloroform: ethanol=1:1) to give 107 mg (65%) of 3-acetylthio-1-(thiazolin-2-yl) azetidine [Compound (4)].

$^1$H-NMR(CDCl$_3$) δ:2.333 (s, 3 H), 3.352 (t, 2 H, J=7.26 Hz), 3.885 (dd, 2 H, J=8.24, 5.28 Hz), 4.012 (t, 2 H, J=7.26 Hz), 4.250–4.374 (m, 1 H), 4.426 (t, 2 H, J=8.25 Hz)

Preparation 2:

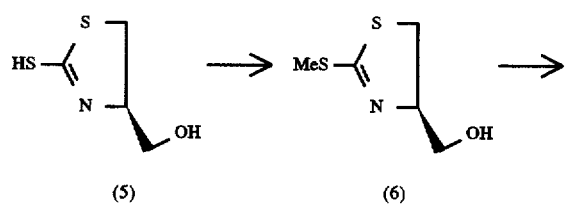

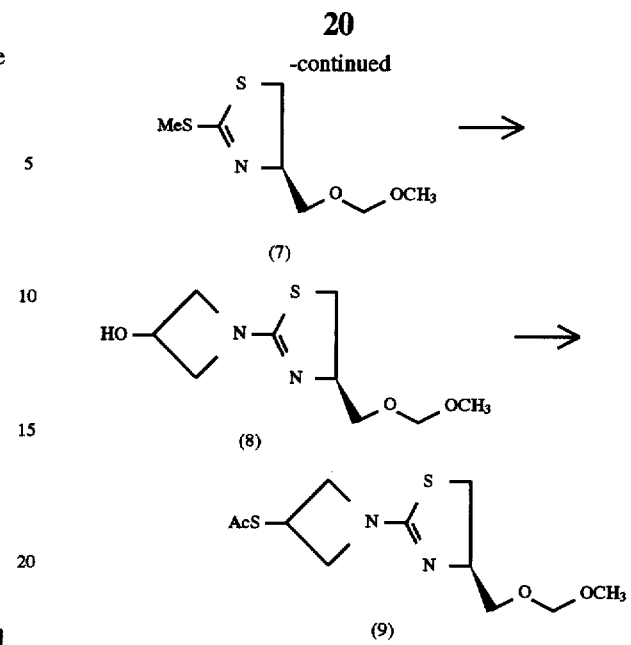

(a) To a mixture solution of 4.88 g of 4(R)-hydroxymethyl-2-mercapto-1,3-thiazoline [Compound (5)] and 22.8 ml of diisopropylethylamine in 65 ml of dry methanol was added 14.00 g of methyl iodide under refluxing condition, and the reaction mixture was refluxed for 1 hour. After removal of the solvent under reduced pressure, the resulting residue was dissolved in ethyl acetate and the organic layer was washed with saturated sodium bicarbonate solution, water and saturated saline solution and dried over magnesium sulfate. The solvent was removed under reduced pressure and the resulting residue was purified by silica gel column chromatography (chloroform-acetone) to give 3.14 g (59%) of 4(R)-hydroxymethyl-2-methylthio-1,3-thiazoline [Compound (6)].

$^1$H-NMR (CDCl$_3$) δ:2.53 (s, 3 H), 3.30 (d d, 1 H, J=8.6, 10.6 Hz),3.44 (dd, 1 H, J=7.6, 10.6 Hz), 3.67–3.73 (m, 1 H), 3.86–3.92 (m, 1 H), 4.51–4.68 (m, 1 H)

(b) 3.14 g of Compound (6) obtained in the step (a) and 6.7 ml of diisopropylethylamine were dissolved in 40 ml of dry dichloromethane solution. 2.33 g of chloromethylmethyl ether was added to the above mixture under ice-cooling and the reaction mixture was stirred for 1 hour under the same condition and for 15 hours at room temperature. After the reaction, the reaction mixture was washed with water, saturated sodium bicarbonate solution and saturated saline solution, and dried over magnesium sulfate. After removal of the solvent, the resulting residue was purified by silica gel column chromatography (chloroform-ethyl acetate) to give 1.42 g (36%) of 4(R)-methoxy-methyloxymethyl-2-methylthio-1,3-thiazoline [Compound (7)].

$^1$H-NMR (CDCl$_3$) δ: 2.55 (s, 3 H), 3.35 (dd, 1 H, J=7.3, 10.9 Hz), 3.38 (s, 3 H), 3.42 (dd, 1 H, J=8.3, 10.9 Hz), 3.474 (dd, 1 H, J=7.6, 9.9 Hz) 3.78 (dd, 1 H, J=5.0, 9.9 Hz), 4.66–4.70 (m, 1 H), 4.67 (s, 2 H)

(c) A mixture solution of 0.924 g of Compound (7) obtained in the above step (b), 0.540 g of 3-hydroxyazetidine. HCl [Compound (1)], 0.490 g of sodium bicarbonate and 0.160 g of acetic acid in 20 ml of ethanol was refluxed for 24 hours. After removal of the solvent, the resulting residue was dissolved in chloroform and washed with 50% potassium carbonate aqueous solution. The organic layer was dried over magnesium sulfate and then removed under reduced pressure. The resulting residue was purified by silica gel column chromatography (10% methanol in chloroform) to give 0.590 g (57%) of 1-(4(R)-methoxymethyloxymethyl-1,3-thiazolin-2-yl)-3-hydroxyazetidine [Compound (8)].

$^1$H-NMR (CDCl$_3$) δ: 3.25–3.32 (m, 1 H), 3.37 (s, 3 H), 3.40–3.46 (m, 1 H), 3.47–3.52 (m, 1 H), 3.63 (dd, 1 H, J=5.3, 9.9 Hz), 3.79–3.89 (m, 2 H),4.16–4.22 (m, 2 H), 4.38–4.45. (m, 1 H), 4.61–4.68 (m, 3 H)

(d) To a solution of 1.40 g of triphenylphosphine in 15 ml of dry tetrahydrofuran was added 0.800 ml of IB diethyl azodicarboxylate under ice-cooling and the mixture solution was stirred for 0.5 hour. Then, a mixture solution of 0.588 g of Compound (8) obtained in the above step (c) and 0.361 ml of thioacetic acid in 15 ml of dry tetrahydrofuran was added dropwise to the above solution under ice-cooling and the reaction mixture was stirred for 1 hour under the same condition and for 1 hour at room temperature. After removal of the solvent, the resulting residue was purified by silica gel column chromatography (chloroform-acetone) to give 0.600 g (82%) of 2-acetyl-thio-1-(4(R)-methoxymethyloxymethyl-1,3-thiazolin-2-yl)azetidine [Compound (9)].

$^1$H-NMR (CDCl$_3$) δ: 2.33 (s, 3 H), 3.29 (dd, 1 H, J=6.3, 10.9 Hz), 3.37 (s, 3 H), 3.43 (dd, 1 H, J=7.6, 10.9 Hz), 3.50 (dd, 1 H, J=7.9, 9.9 Hz), 3.67 (dd, 1 H, J=4.6, 9.9 Hz), 3.86-3.91 (m, 2 H), 4.25–4.34 (m, 1 H), 4.39–4.51 (m, 3 H), 4.66 (s, 2 H)

Preparation 3:

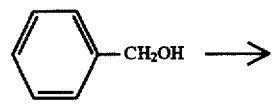

(10)

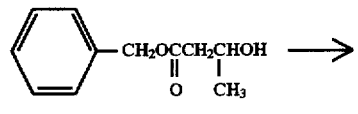

(11)

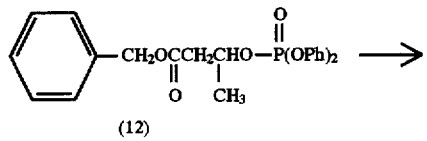

(12)

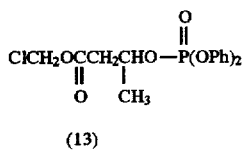

(13)

(a) 0.3 g of sodium hydroxide was added to 64.8 g of benzylalcohol and the reaction mixture was cooled to 0° C. To this reaction mixture was added 12.9 g of β-butyrolactone and the mixture was stirred for 5 minutes at 0° C. and for 2 hours at room temperature. After reaction, the reaction solution was neutralized by adding 15 ml of 1N-HCl solution and the separated organic layer was washed with saturated sodium bicarbonate aqueous solution and saline, and dried over magnesium sulfate. The resulting organic layer was distilled under reduced pressure to give 23.3 g (79%) of benzyl 3-hydroxybutanoate [Compound (11)] as oil.

Boiling point: 134° C./8 mmHg $^1$H-NMR (CDCl$_3$) δ: 1.22 (d, 3 H, J=6.3 Hz), 2.41–2.58 (m, 2 H), 2.95 (brs, 1 H), 4.15–4.24 (m, 1 H), 5.14 (s, 2 H), 7.30–7.36 (m, 5 H)

(b) A mixture solution of 1.0 g of benzyl 3-hydroxybutanoate obtained in the step (a), 1.0 ml of triethylamine and 63 mg of 4-dimethylaminopyridine in 10 ml of methylene chloride was cooled to 0° C. To this solution was added 1.79 g of diphenyl phosphorochloridate under nitrogen atmosphere and the reaction mixture was stirred for 3 hours at room temperature. After reaction, the reaction mixture was washed with 1N-HCl solution, saturated sodium bicarbonate aqueous solution and saline, and dried over magnesium sulfate. The solvent was removed under reduced pressure and the resulting residue was purified by silica gel column chromatography with methylene chloride to give 1.85 g (84%) of 3-diphenoxyphosphoryloxybutanoate [Compound (12)] as colorless oil.

$^1$H-NMR(CDCl$_3$) δ: 1.32 (d, 3 H, J=6.3 Hz), 2.52 (dd, 1 H, J=6.3 Hz, 15.8 Hz), 2.72 (dd, 1 H, J=6.3 Hz, 15.8 Hz), 4.92 (d, 1 H, J=12.9 Hz), 4.98 (d, 1 H, J=12.9 Hz), 4.9–5.1 (m, 1 H), 7.06–7.20 (m, 15 H)

(c) To a solution of 1.23 g of Compound (12) obtained in the step (b), 8 ml of ethyl acetate and 8 ml of ethanol was added 61 mg of 10% palladium-carbon, and the reaction mixture was stirred for 1 hour under H$_2$ gas atmosphere at room temperature. Then, palladium-carbon was filtrated off and the organic layer was removed under reduced pressure. The resulting residue was dissolved in 8 ml of methylene chloride and to this solution was added a mixture of 847 mg of sodium bicarbonate, 8 ml of water, 98 ml of tetrabutylammonium phosphate and 570 mg of chloromethyl chlorosulfonate, and the reaction mixture was stirred for 2 hours at room temperature. After reaction, the organic layer was separated and washed with saline and dried over magnesium sulfate. The solvent was removed under reduced pressure and the resulting residue was purified by silica gel column chromatography with methylene chloride to give 1.10 g (99%) of chloromethyl 3-diphenylphosphoryloxybutanoate [Compound (13)] as colorless oil.

$^1$H-NMR (CDCl$_3$) δ: 1.46 (d, 3 H, J=6.3 Hz), 2.66 (dd, 1 H, J=6.3 Hz, 15.8 Hz), 2.85 (dd, 1 H J=6.3 Hz, 15.8 Hz), 5.09~5.18 (m, 1 H), 5.58 (d, 1 H, J=6.0 Hz), 5.61 (d, 1 H, J=6.0 Hz), 7.16~7.37 (m, 10 H)

Preparation 4:

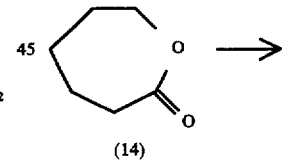

(14)

(15)

(17)

(18)

(a) To a solution of 12.0 g of ε-hexanolactone in 20 ml of ethanol was added a solution of 11.7 g of potassium hydroxide in 20 ml of water under ice-cooling and the reaction mixture was stirred for 2.5 hours at 40° C. After reaction, the reaction mixture was adjusted to pH 9 by adding 1N-HCl solution and washed with ethyl acetate (twice). The aqueous layer was concentrated under reduced pressure and the residue was adjusted to pH 1 by adding 1N-HCl solution and extracted by ethyl acetate. The organic layer was dried over magnesium sulfate and the solvent was removed under reduced pressure to give 11.5 g of 6-hydroxyhexanoic acid. A mixture of 1 g of 6-hydroxyhexanoic acid obtained above, 0.72 mg of sodium bicarbonate in 20 ml of water was stirred for 15 minutes. After reaction, the solvent was removed and the resulting residue was washed with acetonitrile to give 1.24 g of sodibm 6-hydroxyhexanoic acid. Then, 276 mg of this compound was dissolved in 2.7 ml of dimethylformamide and to this solution was added 161 mg of methoxymethyl chloride and the reaction mixture was stirred for 1.5 hours at room temperature. After adding 10 ml of ethyl acetate to the reaction mixture, the organic layer was washed with saline, saturated sodium bicarbonate aqueous solution and saline respectively and dried over magnesium sulfate. The solvent was removed to give 190 mg (59%) of methoxymethyl 6-hydroxyhexanoate [Compound (15)].

$^1$H-NMR(CDCl$_3$) δ: 1.36~1.72 (m, 6 H),2.34 (t, 2 H, J=7.2 Hz), 3.45 (s, 3 H), 4.07 (t, 2 H, J=6.7 Hz), 5.16 (s, 2 H), 5.19 (s, 2 H), 5.22 (s, 2 H), 7.53 (d, 4 H, J=8.7 Hz), 8.23 (d, 4 H, J=8.7 Hz)

(b) To a solution of 25 g of phosphorus trichloride in 70 ml of diethyl ether was added dropwise during 30 minutes a mixture of 51 ml of diisopropylamine and 60 ml of diethyl ether at −10° C., then the reaction mixture was stirred for 1 hour at room temperature. After reaction, unsolved substance was flitrated off and the filtrate was distilled under reduced pressure to give 19.8 g (53%) of phosphorus diisopropylamino dichloride as oil. b.p. 57° C./4 mmHg.

To a solution of 2.06 g of phosphorus diisopropylamino dichloride in 40 ml of methylene chloride was added 4.19 ml of diisopropylamine at −30° C. under nitrogen atmosphere and 3.06 g of p-nitrobenzylalcohol was added. The reaction mixture was stirred for 0.5 hour at the same temperature and further 0.5 hour at room temperature. After removal of the solvent, the resulting residue was dissolved in 40 ml of diethyl ether and washed with saturated saline solution and dried over magnesium sulfate. The solvent was removed to give 4.50 g (100%) of diisopropylamino-di-p-nitrobenzylphosphite [Compound (16)]as yellowish solid.

$^1$H-NMR(CDCl$_3$) δ: 1.23 (d, 12 H, J=6.6 Hz), 3.71 (q, 1 H, J=6.6 Hz), 3.73 (q, 1 H, J=6.6 Hz), 4.75~4.91 (m, 4 H), 7.51 (d, 4 H, J=8.2 Hz), 8.21 (d, 4 H, J=8.2 Hz)

(c) A mixture solution of 100 mg of Compound (15) obtained in the step (a), 87.4 mg of tetrazole and 274 mg of Compound (16) obtained in the step (b) in 10 ml of methylene chloride was stirred for 1.5 hour at room temperature. Then, the reaction mixture was cooled to −40° C. and 215 mg of 3-chloroperbenzoic acid was added to the reaction mixture and the reaction mixture was stirred for 30 minutes. After reaction, the mixture was washed with saturated saline solution, 10% sodium thiosulfate aqueous solution, saturated sodium bicarbonate aqueous solution and saturated saline solution respectively. The organic layer was dried over magnesium sulfate and the solvent was removed under reduced pressure to give 306 mg (95%) of methoxymethyl 6-di-p-nitrobenzyloxy phosphoryloxyhexanoate [Compound (17)].

$^1$H-NMR (CDCl$_3$) δ: 1.36~1.72 (m, 6 H), 2.34 (t, 2 H, J=7.2 Hz), 3.45 (s, 3 H), 4.07 (t, 2 H, J=6.8 Hz), 5.16 (s, 2 H), 5.19 (s, 2 H), 5.22 (s, 2 H), 7.53 (d, 4 H, J=8.7 Hz), 8.23 (d, 4 H, J=8.7 Hz)

(d) To a solution of 206 mg of Compound (17) obtained in the step (c) above in 2 ml of tetrahydrofuran was added 1 ml of 4N-HCl solution and the reaction mixture was stirred for 1.5 hour at room temperature. After reaction, the reaction mixture was adjusted to pH 1 by adding 1N-NaOH solution and washed with diethyl ether. Then, the water layer was adjusted to pH 1 by adding 1N-HCl solution and extracted with ethyl acetate. The organic layer was dried over magnesium sulfate and the solvent was removed to give 96 mg (51%) of 6-di-p-nitrobenzyloxy-phosphoryloxyhexanoic acid. Then, 96 mg of this hexanoic acid was dissolved in 4.8 ml of methylene chloride and to this solution was added a mixture solution of 51.3 mg of sodium bicarbonate in 4.8 ml of water, 6.6 mg of tetrabutylammonium hydrogen sulfate and 40.4 mg of chloromethyl chlorosulfonate, and the reaction mixture was stirred for 1 hour at room temperature. After reaction, the organic layer was separated and washed with saturated sodium bicarbonate aqueous solution and saline, and dried over magnesium sulfate. After removal of the solvent under reduced pressure, the resulting residue was purified by silica gel column chromatography (methylene chloride-acetone) to give 69 mg (55%) of chloromethyl 6-di-p-nitrobenzyloxyphosphoryloxyhexanoate [Compound (18)].

$^1$H-NMR(CDCl$_3$) δ: 1.37~1.71 (m, 6 H), 2.37 (t, 2 H, J=7.2 Hz), 4.07 (t, 2 H, J=6.6 Hz), 5.16 (s, 2 H), 5.19 (s, 2 H), 5.69 (s, 2 H), 7.54 (d, 4 H, J=8.5 Hz), 8.23 (d, 4 H, J=8.5 Hz)

Preparation 5:

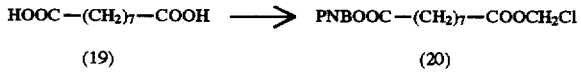

To a solution of 10 g of azelaic acid in 200 ml of acetonitrile were added 16.2 mg of triethylamine and 11.4 g of p-nitrobenzylbromide at nitrogen atmosphere under ice-cooling and the reaction mixture was stirred for 3 hours. After reaction, the reaction mixture was concentrated and 100 ml of water was added. The solution was adjusted to pH 2 by adding 1N-HCl solutionsand extracted 50 ml of ethyl acetate (twice). The organic layer was washed with saturated saline solution and dried over magnesium sulfate. The solvent was removed under reduced pressure and the resulting residue was purified by silica gel column chromatography (methylene chloridemethanol) to give 4.51 g (26%) of mono-p-nitrobenzylazelate. Then, to a solution of 550 mg of this azelate in 10 ml of methylene chloride were added 428 mg of sodium bicarbonate in 10 ml of water. 57 mg of tetrabutylammonium hydrogen sulfate and 336 mg of chloromethyl chlorosulfonate, and the reaction mixture was stirred vigorously for 2 hours at room temperature. After reaction, the reaction mixture was washed with saturated sodium bicarbonate aqueous solution and saturated saline solution, and dried over magnesium sulfate. After removal of the solvent, the resulting residue was purified by silica gel column chromatography (methylene chloride) to give 450 mg (74%) of p-nitrobenzyl chloromethylazelate [Compound (20)].

$^1$H-NMR(CDCl$_3$) δ: 1.20~1.40 (m, 10 H), 2.37 (t, 2 H, J=7.3 Hz), 2.39 (t, 2 H, J=7.2 Hz), 5.20 (s, 2 H), 5.70 (s, 2 H), 7.51 (d, 2 H, J=8.7 Hz), 8.23 (d, 2 H, J=8.7 Hz)

Preparation 6:

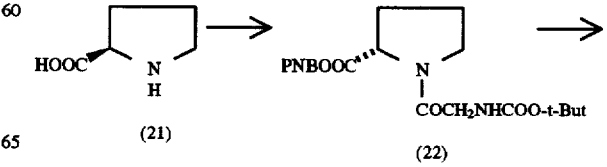

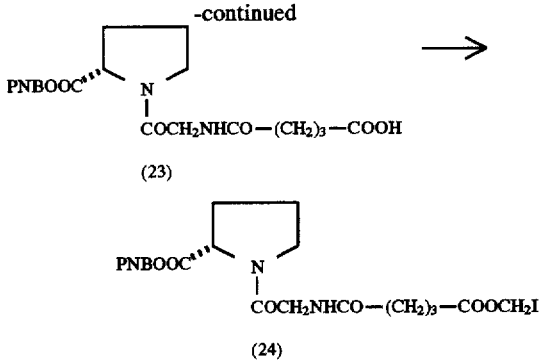

(a) A mixture solution of 5.0 g of L-proline, 9.91 g of p-toluenesulfonic acid monohydrate and 6.65 g of p-nitrobenzyl alcohol in 100 ml of benzene was refluxed for 2 days by using Dean-Stark trap. After reaction, the solvent was removed under reduced pressure and the resulting residue was washed with diethyl ether to give 21.7 g of L-proline p-nitrobenzyl ester p-toluenesulfonic acid salt as oil. Then, a mixture solution of 12.17 g of Boc-glycine and 13.32 g of 1-ethyl-3-(3-dimethylaminopropyl)carbodiimide.hydrochloride in 150 ml of ethylene chloride was stirred for 25 minutes under ice-cooling at nitrogen atmosphere. To this reaction mixture was added a solution of 29.36 g of the compound obtained above in 100 ml ethylene chloride and the reaction mixture was stirred overnight at room temperature. After reaction, the reaction mixture was washed with 10% citric acid aqueous solution, 4% sodium bicarbonate aqueous solution and saline, and dried over magnesium sulfate. The solvent was removed under reduced pressure and the resulting residue was purified by silica gel column chromatography (chloroform-methanol) to give 8.00 g of [N-(t-butoxycarbonyl)glycyl]L-proline p-nitrobenzyl ester [Compound (22)].

$^1$H-NMR(CDCl$_3$) δ: 1.45 (s, 9 H), 1.96~2.33 (m, 4 H), 3.43~3.70 (m, 2 H), 3.93~4.01 (m, 2 H), 4.59 (dd, 1 H, J=4.0 Hz, 8.6 Hz), 5.23 (d, 1 H, J=13.5 Hz), 5.30 (d, 1 H, J=13.5 Hz), 5.37 (br, 1 H), 7.52 (d, 2 H, J=8.9 Hz), 8.23 (d, 2 H, J=8.9 Hz)

(b) To a solution of 4.10 g of Compound (22) obtained in the step (a) in 5 ml of methylene chloride was added 2.5 ml of trifluoroacetic acid under ice-cooling and the reaction mixture was stirred for 1 hour, then, 4 ml of trifluoroacetic acid was added to the reaction mixture and the stirring was continued for 2 hours. After reaction, the solvent was removed to give 5.82 g of glycyl-L-proline p-nitrobenzyl ester trifluoroacetic acid salt as pale brownish oil.

Then, to an ice-cooled solution of 5.54 g of the compound obtained above and 1.499 g of glutaric anhydride in 50 ml of methylene chloride was added 1.83 ml of triethylamine, and the reaction mixture was stirred for 20 minutes at the same temperature. After reaction, 60 ml of 10% citric acid aqueous solution and 200 ml of ethyl acetate were added to the reaction mixture and the organic layer was separated. The organic layer was extracted with 300 ml of 4% sodium bicarbonate aqueous solution, and the extraction was adjusted to pH 4 and extracted with ethyl acetate. The organic solvent was removed under reduced pressure to give 3.43 g of [N-(4-carboxybutanoyl)glycyl]-L-prolin p-nitrobenzyl ester [Compound (23)] as pale yellowish oil.

$^1$H-NMR (CDCl$_3$) δ: 1.90~2.20 (m, 3 H), 1.97 (quintet, 2 H, J=7.3 Hz), 2.20~2.34 (m, 1 H) 2.41 (t, 2 H, J=7.3 Hz), 2.44 (t, 2 H, J=7.3 H z), 3.53~3.75 (m, 2 H), 4.04 (dd, 1 H, J=4.3 H z, 17.5 Hz), 4.22 (dd, 1 H, J=4.9 Hz, 17.5 Hz), 4.58 (dd, 1 H, J=4.0 Hz, 8.9 Hz), 5.20 (d, 1 H J=13.5 Hz), 5.32 (d, 1 H, J=13.5 Hz), 6.85 (br, 1 H), 7.50 (d, 2 H, J=8.6 Hz), 8.22 (d, 2 H, J=8.6 Hz)

(c) To a solution of 3.09 g of Compound (23) obtained in the step (b) in 70 ml of methylene chloride were added 1.85 g of sodium bicarbonate in 70 ml of water, 249 mg of tetrabutylammonium hydrogen sulfate and 1.57 g of ClCH$_2$SO$_3$Cl, and the reaction mixture was stirred for 140 minutes at room temperature. After reaction, the organic layer was separated and washed with 4% sodium bicarbonate aqueous solution and saline, and dried over magnesium sulfate. The solvent was removed under reduced pressure to give 3.00 g of [N-(4-chloromethyloxycarbonylbutanoyl)glycyl]-L-proline p-nitrobenzyl ester as pale yellowish oil. Then, a mixture solution of 2.86 g of the compound obtained above and 1.83 g of sodium iodide in 20 ml of acetonitrile was refluxed for 2 hours. After reaction, the solvent was removed and the resulting residue was dissolved in 70 ml of ethyl acetate. The organic layer was washed with 0.1 N sodium thiosulfate aqueous solution and saline, and dried over magnesium sulfate. The solvent was removed under reduced pressure and the resulting residue was purified by silica gel column chromatography (methylene chloride-acetone) to give 2.35 g of [N-(4-iodomethyloxycarbonylbutanoyl)glycyl]-L-proline P-nitrobenzyl ester [Compound (24)] as yellowish oil.

$^1$H-NMR(CDCl$_3$) δ: 1.92~2.17 (m, 5 H),2.17~2.37 (m, 1 H), 2.33 (t, 2 H, J=7.3 Hz), 2.42 (t, 2 H, J=7.3 Hz), 3. 46~3.74 (m, 2 H), 4.02 (d d, 1 H, J=4.0 Hz, 17.8 Hz), 4.12 (dd, 1 H, J=4.3 Hz, 17.8 Hz), 4.59 (cid, 1 H, J=4.0 Hz, 8.9 Hz), 5.24 (d, 1 H, J=13.5 Hz), 5.32 (d, 1 H, J=13.5 Hz), 5.91 (s, 2 H), 6.45 (br, 1 H), 7.53 (d, 2 H, J=8.9 Hz), 8.24 (d, 2 H; J=8.9 Hz)

EXAMPLE 1

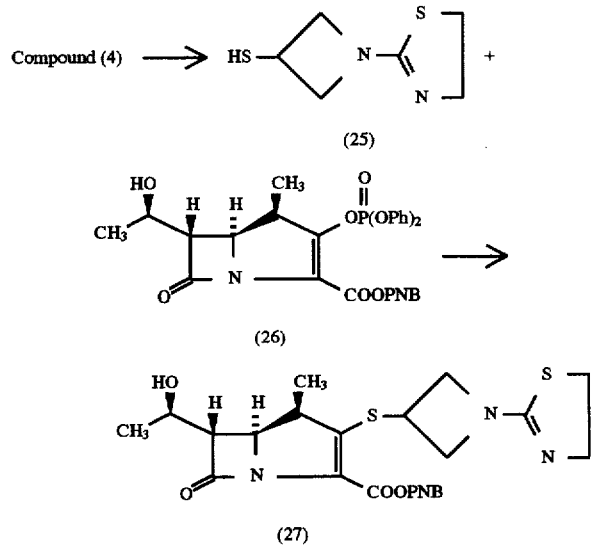

770 mg of 28% sodium methoxide-methanol solution was added to a mixture solution of 862 mg of Compound (4) obtained in the step (c) of Preparation 1 in 20 ml of anhydrous methanol under ice-cooling and nitrogen gas stream. Then the reaction mixture was stirred for 10 minutes under the same conditions. After reaction, 4 ml of 2N-HCl was added to the reaction mixture and the solvent was removed under reduced pressure to give the crude Compound (25). Then, the crude Compound (25) was dissolved in the mixture solution of anhydrous acetonchloroform and to this solution were dded 2430 mg of p-nitrobenzyl (1R, 5S,6S)-2-(diphenylphosphoryloxy)-6-[(R)-1-hydroxyethyl]-1-methyl-carbapen-2-em-3-carboxylate [Compound (26)] and 2.8 ml of diisopropylethylamine under ice-cooling and nitrogen gas stream. After stirring the reaction mixture for 2 hours under the same conditions, ethyl acetate was added and the separated organic layer was washed with saturated sodium bicarbonate aqueous solution and saturated saline solution. The solvent was removed and the resulting residue was purified by silica gel column chromatography with chloroform: aceton (1:2) to give 1339 mg (65% from Compound (4)) of p-nitrobenzyl (1R,5S,6S)-2-[1-(thiazolin-2-yl)azetidin-3-yl]-thio-6-[(R)-1-hydroxyethyl]-1-methyl-carbapen-2-em-3-carboxylate [Compound (27)].

¹H-NMR (CDCl₃) δ: 1.235 (d, 3 H, J=7.26 Hz), 1.349 (d, 3 H, J=6.27 Hz), 3.160 (quintet, 1 H, J=7.26 Hz), 3.265 (dd, 1 H, J=2.3, 6.26 H z), 3.367 (t, 2 H, J=7.26 Hz), 3.898–4.038 (m, 4 H), 4.071–4.147 (m, 1 H), 4.212–4.278 (m, 2 H), 4.372 (2 H, J=7.92 Hz), 5.255 & σ 5.517 (d (AB), 2 H, J=13.85 Hz), 7.665 (d, 2 H, J=8.58 Hz), 8.226 (d, 2 H, J=8.58 Hz)

EXAMPLE 2

Compound (27) ⟶

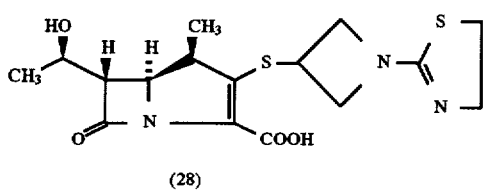

(28)

To a mixture solution of 1339 mg of Compound (27) obtained in Example 1 in 2 ml of tetrahydrofuran were added 60 ml of 0.38 M phosphate buffer solution and 11.2 g of zinc powder, and the reaction mixture was vigorously stirred for 2 hours. After the reaction, unsolved substance was removed by using Celite® and the filtrate was washed with ethylacetate and the pH of the filtrate was adjusted to 5.5. Then, the filtrate was concentrated and the resulting residue was purified by using Diaion HP-4OR column (5% isopropylalcohol-water) to give 630 mg (64%) of (1R,5S,6S)-2-[1-(thiazolin-2-yl)azetidin-3-yl]thio-6-[(R)-1-hydroxyethyl]-1-methylcarbapen-2-em-3-carboxylic acid [Compound (28)].

¹H-NMR (D₂O) δ: 1.093 (d, 3 H, J=6.93 Hz), 1.207 (d, 3 H, J=6.27 Hz), 3.05–3.20 (m, 1 H), 3.357 (dd, 1 H, J=2.3, 5.94 Hz), 3.558 (t, 2 H, J=7.26 Hz), 3.920 (t, 2 H, J=7.26 Hz), 4.00–4.20 (m, 5 H), 4.20–4.30 (m, 1 H), 4.60–4.70 (m, 1 H)

IR(KBr): 1740, 1640, 1590 cm⁻¹

EXAMPLE 3

Compound (9) ⟶

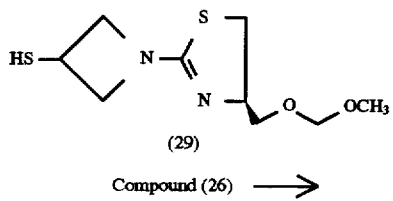

(29)

Compound (26) ⟶

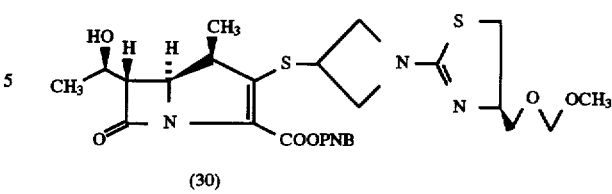

(30)

To a solution of 600 mg of Compound (9) obtained in the step (d) in Preparation 2 in 10 ml of anhydrous methanol was added 400 mg of 28% sodium methoxide-methanol solution under ice-cooling and nitrogen atmosphere, and the reaction mixture was stirred for 5 minutes under the same conditions. After the reaction, 0.355 ml of acetic acid was added and the solvent was removed under reduced pressure. The resulting residue was dissolved in 5 m of anhydrous acetonitrile and the unsolved substance was removed by filtration. Then, this filtrate was added to a solution of 1.230 g of p-nitrobenzyl (1R,5S,6S)-2-(diphenylphosphoryloxy)-6-[(R)-1-hydroxyethyl]-1-methyl-carbapen-2-em-3-carboxylate [Compound (26)] in 5 ml of anhydrous acetonitrile under ice-cooling, and 2.2 ml of diisopropylethylamine was further added dropwise to the reaction mixture. After stirring the reaction mixture for 1.5 hour under the same condition. The solvent was removed under reduced pressure. The resulting residue was dissolved in ethyl acetate and the organic layer was washed with saturated sodium bicarbonate aqueous solution, and dried over magnesium sulfate. After removal of the solvent, the resulting residue was purified by silica gel column chromatography (chloroform-acetone) to give 0.788 g (64% from Compound (26)) of p-nitrobenzyl (1R,5S,6S)-2-[1-(4(R)-methoxymethyloxymethyl-1,3-thiazolin-2-yl)azetidin-3-yl]thio-6-[(R)-1-hydroxyethyl]-1-methyl-carbapen-2-em-3-carboxylate [Compound (30)].

¹H-NMR (CDCl₃) δ: 1.24 (d, 3 H, J=7.3 Hz), 1.36 (d, 3 H, J=6.3 Hz), 3.16 (dq, 1 H, J=7.3, 9.2 Hz), 3.25–3.34 (m, 2 H), 3.37 (m, 2 H), 3.43–3.47 (m, 1 H), 3.51 (dd, 1 H, J=7.9, 9.9 Hz), 3.67 (dd, 1 H, J=5.0, 9.9 Hz), 2.94–4.00 (m 2 H), 4.07–4.17 (m, 1 H), 4.23 (dd, 1 H, J=2.6, 9.2 Hz), 4.20–4.30 (m, 1 H), 4.30–4.51 (m, 3 H), 4.66 (s, 2 H), 5.25 (d, 1 H, J=13.9 Hz), 5.51 (d, 1 H, J=13.9 Hz), 7.66 (d, 2 H, J=8.6 Hz), 8.23 (d, 2 H, J=8.6 Hz)

EXAMPLE 4

Compound (30) ⟶

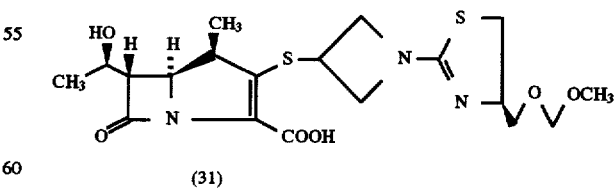

(31)

To a solution of 756 mg of Compound (30) obtained in Example 3 in 10 ml of tetrahydrofuran and 30 ml of 0.35 M phosphate buffer (pH 6.0) solution was added 6.0 g of zinc powder, and the reaction mixture was stirred for 2 hours at room temperature. After removal of the zinc powder by filtration, the filtrate was washed with ethyl acetate and the pH of the filtrate was adjusted to 5.5, then the filtrate was concentrated. The resulting residue was purified by using Diaion HP-40R column (10% isopropanol-water) to give 415 mg (71%) of (1R,5S,6S)-2-[1-((4R)-methoxymethyloxymethyl-1,3-thiazolin-2-yl)azetidin-3-yl]thio-6-[(R)-1-hydroxyethyl]-1-methyl-carbapen-2-em-3-carboxylic acid [Compound (31)].

$^1$H-NMR (D$_2$O) δ: 1.10 (d, 3 H, J=7.3 Hz), 1.21 (d, 3 H, J=6.6 Hz), 3.06–3.18 (m, 1 H), 3.22–3.33 (m, 1 H), 3.33 (s, 3 H), 3.36–3.47 (m, 1 H), 3.61–3.75 (m, 3 H), 4.09–4.31 (m, 6 H), 4.33–4.56 (m, 1 H), 4.60–4.68 (m, 3 H) IR(KBr): 1785, 1640, 1580 cm$^{-1}$

EXAMPLE 5

Compound (28) ——>

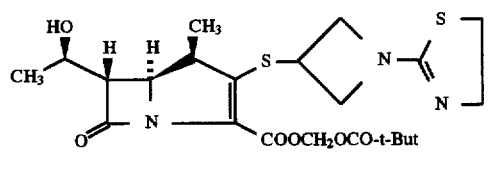

(32)

A mixture solution of 430 mg (1.12 mM) of Compound (28) obtained in the Example 2 and 94.1 mg (1.12 mM) of sodium bicarbonate in 15 ml of water was lyophilized. The resulting amorphous solid was dissolved in 5 ml of dimethylformamide, and 285 mg (1.18 mM) of pivalic acid iodomethyl ester was added to this solution and the reaction mixture was stirred for 1 hour at room temperature. After reaction, ethyl acetate was added to the reaction mixture and the organic layer was washed with saturated sodium bicarbonate aqueous solution and saline, and dried over magnesium sulfate. After removal of the solvent, the resulting residue was purified by silica gel column chromatography (10% methanol-chloroform) to give 415 mg of (74.6%) of pivaloyloxymethyl (1R,5S,6S)-2-[1-(1,3-thiazolin-2-yl)azetidin-3-yl]thio-6-[(R)-1-hydroxyethyl]-1-methyl-carbapen-2-em-3-carboxylate [Compound (32)].

$^1$H-NMR (CDCl$_3$) δ: 1.229 (s, 9 H), 1.229 (d, 3 H, J=7.3 Hz), 1.339 (d, 3 H, 6.3 Hz), 3.165 (dd, 1 H, J=7.3 Hz, 9.2 Hz),3.227 (dd, 1 H, J=2.6 Hz, 6.9 Hz), 3.369 (t,2 H, 7.3 Hz),3.952 (dd, 2 H, 5.6 Hz, 8.6 Hz), 3.988–4.043 (m, 2 H), 4.0854–4.162 (m, 1 H), 4.183–4.274 (m, 2 H), 4.346–4.426 (m, 2 H), 5.842 (d, 1 H, J=5.6 H z), 5.972 (d, 1 H, J=5.6 Hz)

EXAMPLE 6

Compound (28) ——>

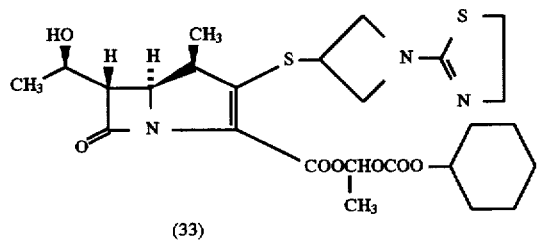

(33)

A mixture solution of 500 mg (1.30 mM) of Compound (28) obtained in the Example 2 and 109.4 mg (1.30 mM) of sodium bicarbonate in 15 ml of water was lyophilized. The resulting amorphous solid was dissolved in 5 ml of dimethylformamide, and 379.5 mg (1.30 mM) of 1-iodoethylcyclohexylcarbonate [prepared by the method discribed in The Journal of Antibiotics, vol. XL, No. 1, page 81] was added to this solution, and the reaction mixture was stirred for 2 hours at room temperature. After reaction, ethyl acetate was added to the reaction mixture and the organic layer was washed with saturated sodium bicarbonate aqueous solution and saline, and dried over magnesium sulfate. The solvent was removed under reduced pressure and the resulting residue was purified by silica gel column chromatography (10% methanol-chloroform) to give 309 mg of (43%) of 1-[(cyclohexyloxy)carbonyloxy]ethyl (1R,5S,6S)-2-[1-(1,3-thiazolin-2-yl)azetidin-3-yl]thio-6-[(R)-1-hydroxyethyl]-1-methylcarbapen-2-em-3-carboxylate [Compound (33)].

$^1$H-NMR(CDCl$_3$) δ: 1.219 (d, 3 H, J=7.3 Hz), 1.323 (d, 3 H, J=6.3 Hz), 1.37~1.50 (m, 2 H), 1.563 (d, 1.5 H, J=5.3 Hz), 1.611 (d, 1.5 H, J=5.3 Hz), 1.67~1.82 (m, 4 H), 1.90~2.05 (m, 4 H), 3.20 (m, 1 H), 3.216 (dd, 1 H, J=2.7 Hz, 6.9 Hz), 3.367 (t, 2 H, J=7.6 Hz), 3.92~4.04 (m, 4 H), 4.08~4.25 (m, 3 H), 4.34~4.43 (m, 2 H), 4.59~4.71 (m, 1 H), 6.880 (q, 0.5 H, J=5.3 Hz), 6.890 (q, 0. 5 H, J=5.3 Hz)

EXAMPLE 7

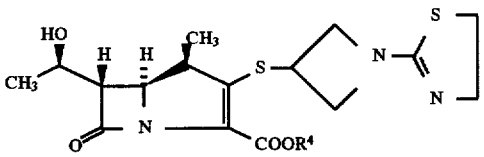

Other ester compounds of (1R,5S,6S)-2-[1-(1,3-thiazolin-2-yl)azetidin-3-yl]thio-6-[(R)-1-hydroxyethyl]-1-methyl-carbapen-2-em-3-carboxylic acid represented by the above formula were obtained by reacting Compound (28) with Compound (18) [obtained in the Preparation 4], Compound (20) [obtained in the Preparation 5] and Compound (24) [obtained in the Preparation 6] respectively.

EXAMPLE 8

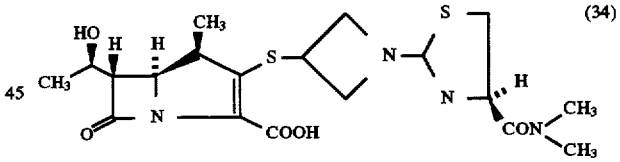

(34)

Compound (34) was obtained in substantially the same manner as that of Examples 1 and 2.

$^1$H-NMR (D$_2$O) δ: 1.16 (d, 3 H, J=6.9 Hz), 1.27 (d, 3 H, J=6.3 Hz), 2.95 (s, 3 H), 3.11 (s, 3 H), 3.19 (m, 1 H), 3.41 (dd, 1 H, J=2.5 Hz, 6.1 1 H z), 3.57 (dd, 1 H, J=5.9 Hz, 11.5 Hz), 3.89 (d d, 1 H, J=8.6 Hz, 11.5 Hz), 4.11~4.37 (m, 5 H), 4.62~4.80 (m, 2 H), 5.37 (dd, 1 H, J=5.9 Hz, 8.6 Hz)

The carbapenem compounds according to the present invention may be formulated in various preparation forms. Formulation Example 1 (Injection):

| (1) Injectable suspension: | |
| --- | --- |
| Compound (28) | 25.0 g |
| Methyl cellulose | 0.5 g |
| Polyvinyl pyrrolidone | 0.05 g |
| Methyl p-oxybenzoate | 0.1 g |
| Polysolvate 80 | 0.1 g |

-continued

| (1) Injectable suspension: | |
|---|---|
| Lidocaine hydrochloride | 0.5 g |
| Distilled water | to make 100 ml |

The above components were formulated into 100 ml of an injectable suspension.

(2) Lyophilization:

An appropriate amount of distilled water was added to 20 g of the sodium salt of Compound (28) to make a total volume of 100 ml. The above solution (2.5 ml) was filled in vials so as for each vial to contain 500 mg of the sodium salt of Compound (28) and lyophilized. The lyophilized vial was mixed in situ with approximately 3–4 ml of distilled water to make an injectable solution.

(3) Powder:

Compound (28) was filled in an amount of 250 ml in a vial and mixed in situ with about 3–4 ml of distilled water to make an injectable solution.

Formulation Example 2 (Tablets)

| Compound (33) | 25 g |
|---|---|
| Lactose | 130 g |
| Crystalline cellulose | 20 g |
| Corn starch | 20 g |
| 3% aqueous solution of hydroxypropyl cellulose | 100 ml |
| Magnesium stearate | 2 g |

Compound (33), lactose, crystalline cellulose, and corn starch were screened through a 60-mesh sieve, homogenized, and charged into a kneader. A 3% aqueous solution of hydroxypropyl cellulose was added and the mixture was kneaded. The product was granulated by a 16-mesh sieve, dried in air at 50° C., and again granulated by a 16-mesh sieve. Magnesium stearate was added to the granule and mixed. The mixture was tabletted to produce tablets weighing 200. mg each and having an 8 mm diameter.

Formulation Example 3 (Capsules)

| Compound (33) | 25 g |
|---|---|
| Lactose | 125 g |
| Corn starch | 48.5 g |
| Magnesium stearate | 1.5 g |

The above components were finely pulverized and thoroughly mixed to produce a homogeneous mixture. The mixture was filled in gelatin capsules, 0.2 g per capsule, to obtain capsules for oral administration.

Formulation Example 4 (Tablets)

| Compound (32) | 25 g |
|---|---|
| Lactose | 130 g |
| Crystalline cellulose | 20 g |
| Corn starch | 20 g |
| 3% aqueous hydroxypropyl cellulose | 100 ml |
| Magnesium stearate | 2 g |

Compound (32), lactose, crystalline cellulose, and corn starch were screened through a 60-mesh sieve, homogenized, and charged into a kneader. The 3% aqueous solution of hydroxypropyl cellulose was added and the mixture was kneaded. The product was granulated by a 16-mesh sieve, dried in air at 50° C., and again granulated by a 16-mesh sieve. Magnesium stearate was added to the granule and mixed. The mixture was tabletted to produce tablets weighing 200 mg each and having an 8 mm diameter.

Formulation Example 5 (Troche)

| Compound (33) | 200 mg |
|---|---|
| Sugar | 770 mg |
| Hydroxypropyl cellulose | 5 mg |
| Magnesium stearate | 20 mg |
| Flavor | 5 mg |
| | 1,000 mg/troche |

The components were mixed with each other and formulated into troches by punching in conventional manner.

Formulation Example 6 (Capsules)

| Compound (33) | 500 mg |
|---|---|
| Magnesium stearate | 10 mg |
| | 510 mg/capsule |

The components were mixed with each other and filled in conventional hard gelatin capsules.

Formulation Example 7 (Dry Syrup)

| Compound (33) | 200 mg |
|---|---|
| Hydroxypropyl cellulose | 2 mg |
| Sugar | 793 mg |
| Flavor | 5 mg |
| | 1,000 mg |

The above components were mixed with each other and formulated into dry syrups in conventional manner.

Formulation Example 8 (Powders)

| (1) Compound (33) | 200 mg |
|---|---|
| Lactose | 800 mg |
| | 1,000 mg |
| (2) Compound (33) | 250 mg |
| Lactose | 750 mg |
| | 1,000 mg |

The components were mixed with each other and formulated in powders in conventional manner.

Formulation Example 9 (Suppository)

| Compound (33) | 500 mg |
|---|---|
| Witepsol H-12 (Product of Dynamite Noble) | 700 mg |
| | 1,200 mg |

The above components were mixed with each other and formulated into suppositories in conventional manner.

What we claim is:

1. A process for the preparation of a (1R,5S,6S)-2-[1-[1, 3-thiazolin-2-yl)azetidin-3-yl]thio-6-[(R)-1-hydroxyethyl]-1-methyl-carbapen-2-em-3-carboxylic acid derivative of the formula:

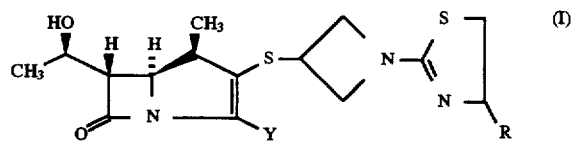

wherein R is hydrogen; lower alkyl group which is optionally substituted by a substituent selected from the group consisting of hydroxy, lower alkoxy and lower alkoxy-lower alkoxy group; —COOR¹ in which R¹ is hydrogen or lower alkyl group; or —CONR²R³ in which R² and R³ are, independently of each other, hydrogen or lower alkyl, and Y is carboxy or protected carboxy, or a pharmaceutically acceptable salt thereof, which comprises reacting a compound of formula:

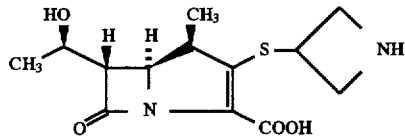

with a compound of formula:

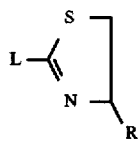

wherein L is a leaving group and R has the same meaning as above to give a compound of formula:

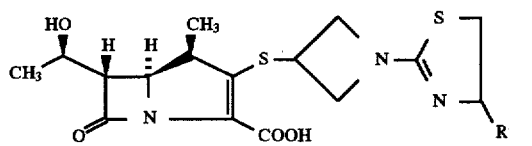

wherein R has the same meaning as above, or a pharmaceutically acceptable salt thereof, and optionally subjecting the resulting compound of formula (VII) to esterification of the carboxy group to give the compound represented by formula (I) wherein Y is a protected carboxy.

2. A process for the preparation of a (1R,5S,6S)-2-[1-(1,3-thiazolin-2-yl)azetiden-3-yl]thio-6-[(R)-1-hydroxyethyl]-1-methyl-carbapen-2-em-3-carboxylic acid derivative of the formula:

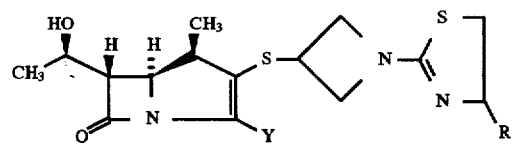

wherein R is hydrogen; lower alkyl group which is optionally substituted by a substituent selected from the group consisting of hydroxy, lower alkoxy and lower alkoxy-lower alkoxy group; —COOR¹ in which R¹ is hydrogen or lower alkyl group; or —CONR²R³ in which R² and R³ are, independently of each other, hydrogen or lower alkyl, and Y is carboxy or protected carboxy, or a pharmaceutically acceptable salt thereof, which comprises reacting a compound of formula:

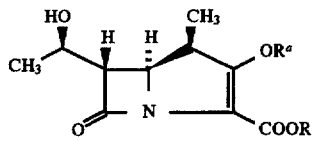

wherein $R^a$ is an acyl group; and R' is a carboxyl protecting group, with a compound of formula:

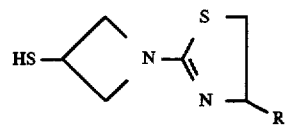

wherein R has the same meaning as above, to give a compound of formula:

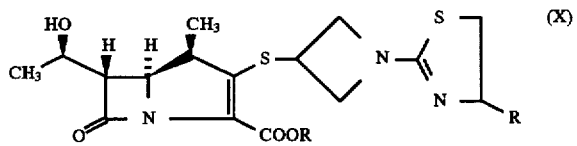

wherein R and R' have the same meanings as above, then, subjecting the resulting compound of formula (X) to removal of the carboxyl protecting group to give a compound of formula:

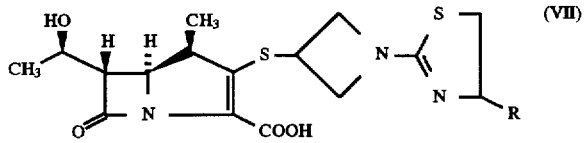

wherein R has the same meaning as above, or a pharmaceutically acceptable salt thereof, and optionally subjecting the resulting compound of formula (VII) to esterification of the carboxy group to give the compound represented by formula (I) wherein Y is a protected carboxy.

* * * * *